United States Patent [19]

Rowson et al.

[11] Patent Number: 4,889,553
[45] Date of Patent: Dec. 26, 1989

[54] HERBICIDES

[75] Inventors: Graham P. Rowson, Hundon; John C. Head, Bishops Stortford, both of England; Jurgen Westermann; Martin Kruger, both of Berlin, Fed. Rep. of Germany; Friedrich Arndt, Berlin, Fed. Rep. of Germany; Richard Rees, Berlin, Fed. Rep. of Germany

[73] Assignee: Schering Agrochemicals, United Kingdom

[21] Appl. No.: 50,733

[22] Filed: May 15, 1987

[30] Foreign Application Priority Data

May 17, 1986 [GB] United Kingdom ............... 12062
Dec. 12, 1986 [GB] United Kingdom ............. 3643021
Mar. 5, 1987 [GB] United Kingdom ............. 3707202
Mar. 12, 1987 [GB] United Kingdom ............. 3708215

[51] Int. Cl.$^4$ .............. A01N 43/653; C07D 249/12; C07D 249/14; C07D 401/04; C07D 403/04; C07D 417/04
[52] U.S. Cl. .................................... 71/92; 71/90; 71/93; 544/212; 544/198; 544/207; 544/209; 544/310; 544/316; 544/317; 544/319; 544/320; 544/321; 544/324; 544/327; 544/331; 544/322; 546/276; 548/135; 548/138; 548/141; 548/264; 548/265; 548/266; 548/267
[58] Field of Search ............. 71/92, 93, 90; 548/263, 548/264, 265, 135, 267, 138, 141, 265, 266; 544/209, 212, 320, 321, 331, 310, 319, 324, 322, 316, 317, 320, 321, 327, 331, 198, 207; 546/276

[56] References Cited

U.S. PATENT DOCUMENTS

| | | | |
|---|---|---|---|
| 3,952,001 | 4/1976 | Brookes et al. | 260/308 R |
| 4,251,262 | 2/1981 | Brookes et al. | 71/92 |
| 4,734,123 | 3/1988 | Monte | 548/263 |

FOREIGN PATENT DOCUMENTS

| | | |
|---|---|---|
| 177897 | 3/1979 | Czechoslovakia . |
| 0244847 | 11/1987 | European Pat. Off. . |
| 0244948 | 11/1987 | European Pat. Off. . |

OTHER PUBLICATIONS

"Triazoles. Part XI. Synthesis of 1,2,4-Triazole-3-Sulphonic Acids by Oxidation of 1,2,4-Triazoline-3-Thiones", A. J. Blackman and J. B. Polya, J. Chem. Soc. (C), 1970, pp. 2403-2409.
Chemical Abstracts, vol. 105, No. 25, Dec. 22, 1986, pp. 781, Abstract No. 226455a, A. M. Abdel-Fattah et al., "Reaction with 1,2,4-Triazoline—5-Thiones".
Chemical Abstracts Entry 92235n, vol. 79, (1973), to Boot Pure Drug Co.

Primary Examiner—John M. Ford
Attorney, Agent, or Firm—Ostrolenk, Faber, Gerb & Soffen

[57] ABSTRACT

Herbicidal triazole sulphonamides of the formula:

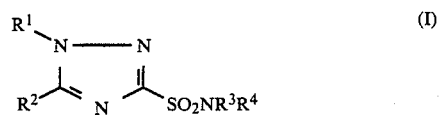

(I)

and salts thereof, where:

$R^1$ represents hydrogen or a substituted or unsubstituted alkyl, alkenyl, alkynyl, cycloalkyl, aryl, aralkyl, acyl, alkoxycarbonyl, aminocarbonyl, sulphonyl or heterocyclic group;

$R^2$ represents hydrogen, halo, cyano, hydroxy, mercapto, a substituted or unsubstituted alkyl, alkenyl, alkynyl, alkoxy, alkylthio, alkylsulphinyl, alkylsulphonyl, acyl, alkoxycarbonyl, aminocarbonyl, aryl or amino group, or a heterocyclic group;

$R^3$ represents a substituted or unsubstituted heterocyclic, benzheterocyclic, aryl or aralkyl group; and $R^4$ represents hydrogen, a substituted or unsubstituted alkyl, alkenyl, alkynyl, acyl, aroyl, alkylsulphonyl, alkoxycarbonyl, aminocarbonyl, aralkyl, or a group of the formula:

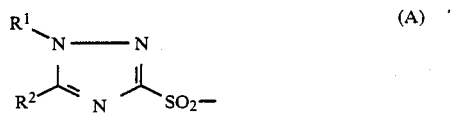

(A)

where $R^1$ and $R^2$ are as defined hereinbefore, processes for their preparation and compositions containing them.

18 Claims, No Drawings

HERBICIDES

This invention concerns herbicidal triazolesulphonamides, processes for their preparation, and compositions containing them.

In one aspect, the invention provides the triazolesulphonamides of the formula:

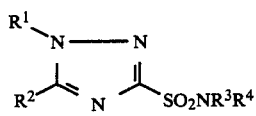  (I)

and salts thereof, where:
$R^1$ represents hydrogen or a substituted or unsubstituted alkyl, alkenyl, alkynyl, cycloalkyl, aryl, aralkyl, acyl, alkoxycarbonyl, aminocarbonyl, sulphonyl or heterocyclic group;
$R^2$ represents hydrogen, halo, cyano, hydroxy, mercapto, a substituted or unsubstituted alkyl, alkenyl, alkynyl, alkoxy, alkylthio, alkylsulphinyl, alkylsulphonyl, acyl, alkoxycarbonyl, aminocarbonyl, aryl or amino group, or a heterocyclic group;
$R^3$ represents a substituted or unsubstituted heterocyclic, benzheterocyclic, aryl or aralkyl group; and
$R^4$ represents hydrogen, a substituted or unsubstituted alkyl, alkenyl, alkynyl, acyl, alkylsulphonyl, alkoxycarbonyl, aminocarbonyl, aralkyl, or a group of the formula:

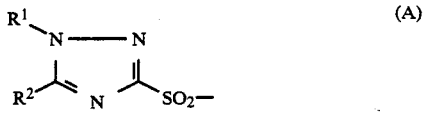  (A)

where $R^1$ and $R^2$ are as defined hereinbefore.

When $R^1$, $R^2$ or $R^4$ represents or contains an alkyl group, that group is preferably of 1 to 6 carbon atoms, especially of 1 to 4 carbon atoms. Specific preferred unsubstituted alkyl or alkyl-containing groups which $R^1$, $R^2$ and $R^4$ may represent include methyl, ethyl, n-propyl, isopropyl, n-butyl, isobutyl, s-butyl and t-butyl. The alkyl group may if desired be substituted, for example by one or more halogen atoms, e.g. fluorine, chlorine or bromine, alkoxy or alkylthio groups of 1 to 4 carbon atoms, e.g. methoxy, ethoxy or methylthio, or acyloxy groups of 2 to 5 carbon atoms. Specific examples of substituted alkyl groups which $R^1$, $R^2$ and $R^4$ may represent include chloromethyl, bromomethyl, dichloromethyl and trifluoromethyl. In addition, $R^2$ may advantageously represent methoxy, ethoxy, n-propoxy, methylthio, hydroxymethyl, methoxymethyl, ethoxymethyl, methoxyethyl, ethoxyethyl or acetoxymethyl.

When $R^1$, $R^2$ or $R^4$ represents an alkenyl or alkynyl group, that group is preferably of 2 to 6 carbon atoms, for example vinyl, allyl or propargyl. Any such alkenyl or alkynyl group is preferably unsubstituted.

When $R^1$ represents cycloalkyl, it is preferably of 5 to 7 carbon atoms, especially cyclopentyl or cyclohexyl.

When $R^1$, $R^2$ or $R^4$ represents an acyl or alkoxycarbonyl group, or an alkyl-substituted aminocarbonyl or sulphonyl group, any alkyl moiety thereof is preferably as described hereinbefore. The acyl group may if desired be an aroyl or heteroaroyl group, especially a benzoyl or 2-thienoyl group. Specific preferred acyl and alkoxycarbonyl groups include acetyl and methoxycarbonyl.

When $R^1$, $R^3$ or $R^4$ represents an aralkyl group, it is preferably benzyl, which may be substituted by one or more alkyl or alkoxy groups of 1 to 4 carbon atoms, halogen atoms or nitro groups.

When $R^1$ is or contains an aryl group, it is preferably a phenyl group which is desirably unsubstituted but which may be substituted, especially 3,5-disubstituted, by one or more halogen atoms or alkyl or alkoxy groups of 1 to 4 carbon atoms, particularly methyl or methoxy groups.

When $R^2$ represents aryl it is preferably phenyl which is desirably unsubstituted but which may be substituted by one or more halogen atoms or alkyl or alkoxy groups of 1 to 4 carbon atoms, particularly methyl or methoxy groups.

When $R^3$ is or contains an aryl group, that group is preferably phenyl, which is desirably substituted, for example by one or more halogen atoms (e.g. fluorine, chlorine or bromine), nitro groups, cyano groups, substituted or unsubstituted amino or amido groups (e.g. alkylamino, dialkylamino, acylamino, alkylamido or dialkylamido groups, especially where the alkyl moiety has from 1 to 4 carbon atoms), optionally-substituted alkyl, alkoxy or alkylthio groups of 1 to 4 carbon atoms (e.g. methyl, ethyl, methoxy, ethoxy, methylthio or ethylthio), alkoxycarbonyl groups of 2 to 5 carbon atoms, or alkylsulphinyl or alkylsulphonyl groups of 1 to 4 carbon atoms.

When $R^1$, $R^2$ or $R^3$ represents a heterocyclic group, that group is preferably a monocyclic group of 5 or 6 ring atoms which contains at least one atom of nitrogen, oxygen or sulphur, and which may of course be substituted, e.g. by one or more halogen atoms, hydroxy groups, nitro groups, cyano groups, optionally-substituted amino or amido groups (e.g. by alkyl of 1 to 4 carbon atoms), alkyl, alkoxy or alkylthio groups of 1 to 4 carbon atoms, acyl or alkoxycarbonyl groups of 2 to 5 carbon atoms, or alkylsulphinyl or alkylsulphonyl groups of 1 to 4 carbon atoms. Included within the possible heterocyclic groups are of course the N-oxides of appropriate heterocycles.

Heterocyclic groups which $R^1$ may represent include substituted or unsubstituted pyridinyl, pyrimidinyl, piperidinyl, pyrazinyl, quinoxalinyl, morpholinyl, triazinyl, thienyl, benzoxazolyl, thiadiazolyl and triazolyl groups.

Specific preferred heterocyclic groups which $R^2$ may represent include pyrrol-1-yl and 2,5-dimethylpyrrol-1-yl.

When $R^2$ represents halo, it is preferably fluoro, chloro or bromo.

When $R^2$ represents a substituted amino group, it is preferably an alkylamino or dialkylamino group in which each alkyl moiety is of 1 to 4 carbon atoms, and may be further substituted, e.g. by alkoxy groups of 1 to 4 carbon atoms. Specific preferred such groups are methylamino, ethylamino, methoxymethylamino, ethoxymethylamino and dimethylamino.

When $R^3$ represents a heterocyclic or benzheterocyclic group, it is preferably a benzothienyl or benzoxazolyl group, though it may also be, for example, a thiazolyl, isoxazolyl, pyridinyl, piperidinyl, triazolyl, benzothiazolyl or quinolinyl group, which may be substituted by one or more alkyl or alkoxy groups of 1 to 4 carbon atoms.

R[1] is preferably hydrogen, alkyl of 1 to 6 carbon atoms, phenyl (which is desirably unsubstituted but which may be substituted, especially 3,5-disubstituted, by one or more halogen atoms or alkyl or alkoxy groups of 1 to 4 carbon atoms, particularly methyl or methoxy groups), or monocyclic heterocyclyl of 5 or 6 ring atoms which contains at least one atom of nitrogen and which is unsubstituted or substituted by one or more alkyl, alkoxy or alkylthio groups of 1 to 4 carbon atoms, cyano groups, amino groups (which may be unsubstituted or substituted e.g. by methyl or ethyl), halogen atoms or alkylsulphinyl or alkylsulphonyl groups of 1 to 4 carbon atoms. Preferred groups which R[1] may represent include hydrogen, methyl, ethyl, n-propyl, n-butyl, phenyl, 3,5-dimethylphenyl, and substituted or unsubstituted pyrimidin-2-yl, 1,3,5-triazin-2-yl and 1,2,4-triazin-3-yl groups, especially 4-methylpyrimidin-2-yl, 4-methoxypyrimidin-2-yl, 4,6-dimethylpyrimidin-2-yl, 4,6-dimethoxypyrimidin-2-yl, 4,6-dichloropyrimidin-2-yl, 4-methyl-6-chloropyrimidin-2-yl, 4-methyl-6-methylaminopyrimidin-2-yl, 4-methyl-6-aminopyrimidin-2-yl, 4-methyl-6-dimethylaminopyrimidin-2-yl, 4-chloro-6-methoxypyrimidin-2-yl, 4-methyl-5-chloro-6-methoxypyrimidin-2-yl, 4-methyl-6-methoxypyrimidin-2-yl, 4,6-dimethoxy-1,3,5-triazin-2-yl, 4-chloro-6-methyl-1,3,5-triazin-2-yl, 4-chloro-6-methoxy-1,3,5-triazin-2-yl, 4-methoxy-6-methyl-1,3,5-triazin-2-yl, 4-methylamino-6-methoxy-1,3,5-triazin-2-yl and 4-methylamino-6-chloro-1,3,5-triazin-2-yl.

R[2] is preferably hydrogen, halo, cyano, alkyl or alkoxy of 1 to 6 carbon atoms (which is unsubstituted or substituted by one or more halogen atoms, hydroxy groups, alkoxy groups of 1 to 4 carbon atoms, or acyloxy groups of 2 to 5 carbon atoms), alkoxycarbonyl of 2 to 5 carbon atoms, amino, alkylamino of 1 to 4 carbon atoms, monocyclic heterocyclyl of 5 or 6 ring atoms which contains at least one atom of nitrogen and which is unsubstituted or substituted by one or more alkyl groups of 1 to 4 carbon atoms. Specific preferred groups which R[2] may represent include hydrogen, chloro, bromo, cyano, methyl, ethyl, n-propyl, n-butyl, s-butyl, hydroxymethyl, methoxymethyl, ethoxymethyl, methoxyethyl, acetoxymethyl, methoxy, ethoxy, methoxycarbonyl, amino, methylamino, ethylamino, pyrrol-1-yl and 2,5-dimethylpyrrol-1-yl R[3] preferably represents a phenyl group which is substituted (especially 2-substituted, 2,6-disubstituted, 2,3,5-trisubstituted, 2,3,6-trisubstituted or 2,3,5,6-tetrasubstituted) by one or more halogen atoms, nitro groups, cyano groups or alkyl, alkoxy or alkylthio groups of 1 to 4 carbon atoms (which may themselves be substituted by one or more halogen atoms) or alkoxycarbonyl groups of 2 to 6 carbon atoms.

Specific groups which R[3] may represent include 2-fluorophenyl, 2-chlorophenyl, 2-bromophenyl, 2-cyanophenyl, 2-methylphenyl, 2-methoxyphenyl, 2-methylthiophenyl, 2-trifluoromethylphenyl, 2-methoxycarbonylphenyl, 2-ethoxycarbonylphenyl, 3-fluorophenyl, 2-difluoromethoxyphenyl, 2,3-difluorophenyl, 2,5-difluorophenyl, 2,6-dimethylphenyl, 2,3,5,6-tetrafluorophenyl, 2-methyl-6-methoxycarbonylphenyl, 2-fluoro-6-methoxycarbonylphenyl, and especially 2,6-difluorophenyl, 2,6-dichlorophenyl, 2,6-dibromophenyl, 2-methyl-6-nitrophenyl, 2-chloro-6-methylphenyl, 2-fluoro-6-methoxycarbonylphenyl, 2-chloro-6-methoxycarbonylphenyl, 2,6-dichloro-3-methylphenyl or 2-chloro-6-fluorophenyl.

R[4] preferably represents hydrogen, methyl, acetyl, benzoyl, methylsulphonyl, methoxycarbonyl, dimethylcarbamoyl or benzyl.

Particularly preferred compounds according to the invention are those of the Examples provided hereinafter, though particular mention may be made of:
N-(2,6-difluorophenyl)-1-(pyrimidin-2-yl)-5-methyl-1,2,4-triazole-3-sulphonamide;
N-(2,6-dichloro-3-methylphenyl)-1-(pyrimidin-2-yl)-5-methyl-1,2,4-triazole-3-sulphonamide;
N-(2-methyl-6-nitrophenyl)-1-(pyrimidin-2-yl)-5-methyl-1,2,4-triazole-3-sulphonamide;
N-(2,6-difluorophenyl)-1-(4,6-dimethylpyrimidin-2-yl)-5-methyl-1,2,4-triazole-3-sulphonamide
N-(2,6-dichlorophenyl)-1-(pyrimidin-2-yl)-5-methyl-1,2,4-triazole-3-sulphonamide;
N-(2,6-difluorophenyl)-1-(4-methylpyrimidin-2-yl)-5-methyl-1,2,4-triazole-3-sulphonamide;
N-(2,6-difluorophenyl)-1-(4-methoxy-6-methylpyrimidin-2-yl)-5-methyl-1,2,4-triazole-3-sulphonamide;
N-(2,6-dichlorophenyl)-1-(4,6-dimethoxy-1,3,5-triazin-2-yl)-5-methyl-1,2,4-triazole-3-sulphonamide;
N-(2,6-dichlorophenyl)-1-(4,6-dimethylpyrimidin-2-yl)-1,2,4-triazole-3-sulphonamide;
N-(2,6-dichlorophenyl)-1-(4,6-dimethylpyrimidin-2-yl)-5-methyl-1,2,4-triazole-3-sulphonamide;
N-(2-methyl-6-nitrophenyl)-1-(4,6-dimethylpyrimidin-2-yl)-5-methyl-1,2,4-triazole-3-sulphonamide;
N-(2,6-dichlorophenyl)-5-(2,5-dimethylpyrrol-1-yl)-1,2,4-triazole-3-sulphonamide;
N-(2,6-difluorophenyl)-5-(2,5-dimethylpyrrol-1-yl)-1,2,4-triazole-3-sulphonamide;
N-(2,6-dichloro-3-methylphenyl)-1-(4,6-dimethylpyrimidin-2-yl)-1,2,4-triazole-3-sulphonamide;
N-(2,6-dichlorophenyl)-5-amino-1-(4,6-dimethylpyrimidin-2-yl)-1,2,4-triazole-3-sulphonamide; and
N-(2,6-dichloro-3-methylphenyl)-5-amino-1-(4,6-dimethoxy-1,3,5-triazin-2-yl)-1,2,4-triazole-3-sulphonamide.

In another aspect, the invention provides a process for the preparation of a triazolesulphonamide of formula I, in which a triazolesulphonyl halide of the formula:

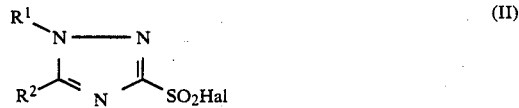

where R[1] and R[2] are as defined hereinbefore, and Hal represents halogen, is reacted in the presence of a base with an amine of the formula R[3]R[4]NH where R[3] and R[4] are as defined hereinbefore to give the desired compound.

The reaction is conveniently effected at a temperature of from −10° C. to 100° C., particularly from −10° C. to 25° C., conveniently at room temperature.

The base is preferably an organic base, especially a tertiary organic base, for example pyridine, N,N-dimethylaniline or triethylamine, or an excess of the amine R[3]R[4]NH. The reaction may be catalysed by certain tertiary organic bases, for example dimethylaminopyridine. Where R[4] is an acyl group, the base employed is preferably a strong base, for example sodium hydride, and the reaction is conveniently effected in a suitable aprotic solvent medium, e.g. tetrahydrofuran.

The reaction conditions may be adjusted if desired to favour the production of compounds of formula I in which $R^4$ represents a group of formula A. When such compounds are desired, it is preferred to employ at least 2 moles of the sulphonyl halide of formula II per mole of the amine. Alternatively, the compounds of formula I where $R^4$ represents a group of formula A may be prepared from the corresponding compounds of formula I where $R^4$ represents hydrogen by reaction thereof in the presence of a strong base with further sulphonyl halide of formula II. In such a case, the base may, for example, be sodium hydride employed in a suitable solvent medium, e.g. tetrahydrofuran.

The compounds of formula II may themselves be prepared by reacting a compound of the formula:

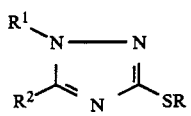
(III)

where $R^1$ and $R^2$ are as defined hereinbefore, and R represents hydrogen, alkenyl, acyl or aralkyl, with the appropriate halogen or sulphuryl halide in a suitable solvent medium, to give the desired compound.

The reaction is desirably effected with cooling to less than ambient temperature, e.g. to a temperature of 5° C. or less.

The compounds of formula III where R represents hydrogen may themselves be prepared by a process in which an alkanoylthiosemicarbazide of the formula

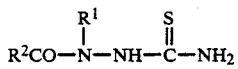
(IV)

where $R^1$ and $R^2$ are as defined hereinbefore is cyclised in the presence of a base to give the desired compound.

The cyclisation is preferably effected by heating the compound of formula IV in water.

The base employed may, for example, be a carbonate, e.g. sodium carbonate.

The compounds of formula III where R is other than hydrogen may each be prepared from the corresponding compound where R is hydrogen by methods known per se, for example alkylation and acylation.

The compounds of formula III may also be interconverted by other methods known per se in order to give any desired starting material of that formula. For example, when R is a protecting group, for example benzyl, the compounds where $R^1$ or $R^2$ is hydrogen may be converted into corresponding compounds where $R^1$ or $R^2$ is other than hydrogen by known anion coupling techniques.

The compounds of formula IV may be prepared by acylation of the corresponding thiosemicarbazides of the formula $R^1NH.NH.CS.NH_2$ where $R^1$ is as defined hereinbefore by methods known per se.

The compounds of formula I may also be interconverted by methods known per se. For example, the compounds of formula I in which $R^4$ is other than hydrogen may in general be prepared from the corresponding compounds of formula I where $R^4$ is hydrogen by reaction thereof in the presence of a base, for example sodium hydride, potassium carbonate or pyridine, with a halide of formula $R^4Hal$.

The compounds of formula I in which $R^4$ represents a group of formula A may be hydrolysed under appropriate conditions to give the corresponding compounds in which $R^4$ is hydrogen.

The compounds of formula I in which $R^1$ is other than hydrogen may be prepared from the corresponding compounds of formula I where $R^1$ is hydrogen by reaction thereof with an appropriate electrophile (for example a compound of formula $R^1Hal$, $R^1SO_2CH_3$ or $R^1SO_2p$-toluene), in the presence, if desired, of a base such as sodium hydride, potassium carbonate, triethylamine or 1,8-diazabicyclo(5,4,0)undec-7-ene, at room temperature or with heating and in a suitable solvent medium, e.g. dimethylformamide, tetrahydrofuran or dimethoxyethane.

Carboxy groups present in the compounds of formula I may be esterified, ester or acyl groups present may be hydrolysed to give the corresponding acids, and cyano or ester groups may be converted to amido or substituted amido groups. Such transformations, as well as many others, may be effected by techniques well-known to those skilled in the art, and various examples of such transformations are provided hereinafter.

The compounds of formula I are herbicidally-active against a wide range of broad-leaved and grassy weeds, but are comparatively safe to certain crop species. They may thus be of use as selective herbicides, particularly in the control of a range of weeds in cereals or other crops, e.g. wheat, barley, maize, soya beans, oilseed rape, cotton or sunflowers.

In another aspect, the invention provides a herbicidal composition which comprises one or more compounds of the invention in association with a suitable carrier and/or surface active agent.

The compositions usually contain from 0.01 to 99% by weight of the present compounds, and are normally produced initially as concentrates containing from 0.5 to 99%, preferably from 0.5 to 85%, and especially from 10 to 50% by weight thereof. Such concentrates are diluted if necessary before application to the locus to be treated such that the active ingredient comprises from 0.01 to 5% by weight of the formulation applied.

The carrier may be water, in which case an organic solvent may also be present, though this is not usually employed. A flowable suspension concentrate may be formed by grinding the compound with water, a wetting agent and a suspending agent, e.g. xanthan gum.

The carrier may alternatively be a water immiscible organic solvent, e.g. a hydrocarbon which boils within the range 130°–270° C., e.g. xylene, in which the compound is dissolved or suspended. An emulsifiable concentrate containing a water immiscible solvent may be formed with a surface active agent so that the concentrate acts as a self-emulsifiable oil on admixture with water.

The carrier may alternatively be a water-miscible organic solvent e.g. 2-methoxy ethanol, methanol, propylene glycol, diethylene glycol, diethylene glycol monoethyl ether, methylformamide or dimethylformamide.

The carrier may alternatively be a solid, which may be finely divided or granular. Examples of suitable solids are limestone, clays, sand, mica, chalk, attapulgite, diatomite, perlite, sepiolite, silicas, silicates, ligno-sulphonates and solid fertilizers. The carrier can be of natural or synthetic origin or can be modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant, e.g. a polyhalogenated alkane such as dichlorofluoromethane, and suitably also with a solvent.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with a fatty alcohol ethoxylate, or salts of such esters, fatty alcohol sulphates such as sodium dodecyl sulphate, ethoxylated fatty alcohol sulphates, ethoxylated alkylphenol sulphates, lignin sulphates, petroleum sulphonates, alkylaryl sulphonates such as alkyl-benzene sulphonates or lower alkylnaphthalene sulphonates, salts of sulphonated naphthaleneformaldehyde condensates, salts of sulphonated phenolformaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The surface active agents may also comprise non-ionic agents, for example condensation products or fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethyl-ammonium bromide, or ethoxylated tertiary fatty amines.

Preferred surface active agents include ethoxylated fatty alcohol sulphates, lignin sulphonates, alkyl-aryl sulphonates, salts of sulphonated naphthaleneformaldehyde condensates, salts of sulphonated phenolformaldehyde condensates, sodium oleoyl N-methyltauride, dialkyl sulphosuccinates, alkyl phenol ethoxylates, and fatty alkyl ethoxylates.

The present active compounds, especially those of the Examples provided hereinafter, and particularly those specifically identified hereinbefore, may be admixed with another pesticide, e.g. a herbicide, fungicide or insecticide, or a plant growth regulator, particularly another herbicide e.g. trietazine, linuron, MCPA, dichlorprop, isoxaben, diflufenican, metolachlor, fluometuron, oxyfluorfen, fomesafen, bentazone, prometryne, norflurazon, clomazone, EPTC, imazaquin, and especially isoproturon, methabenzthiazuron, trifluralin, ioxynil, bromoxynil, benazolin, mecoprop, fluroxypyr, alachlor, acifluorfen, lactofen, metribuzin and pendimethalin.

The present compounds may be applied to plants, the soil, land or aquatic areas, and particularly to a locus at which a crop is growing or is about to grow. The compounds are active both pre- and post-emergence.

The invention is illustrated by the following Examples, in which Me=methyl, Et=ethyl, Pr=propyl, Bu=butyl and Ph=phenyl:

PREPARATIVE EXAMPLE A

N-(2,6-difluorophenyl)-1-phenyl-5-n-propyl-1,2,4-triazole-3-sulphonamide (Compound A1)

(a) 1-Butyryl-1-phenylthiosemicarbazide

A stirred mixture of 1-phenylthiosemicarbazide (30 g) and butyric anhydride (31.2 g) in toluene (250 ml) was heated under reflux for 2 hours. After cooling, crude product was filtered off as a white powder, mp 219°–221° C.

(b) 3-Mercapto-1-phenyl-5-propyl-1,2,4-triazole

A suspension of the product of stage (a) (40 g) in aqueous 10% sodium carbonate solution (200 ml) was heated under reflux for 2 hours. The clear yellow solution obtained was cooled and acidified with concentrated hydrochloric acid to afford an off-white precipitate. This was filtered off and recrystallised from ethanol to give the desired product (33 g), as white needles, mp 142°–143° C.

(c) 1-Phenyl-5-propyl-1,2,4-triazole-3-sulphonyl chloride

Chlorine gas was bubbled through a stirred suspension of the product of stage (b) (20 g) in 60% aqueous acetic acid (200 ml) for 90 minutes at −5° C. The white solid was filtered off, washed with ice-cold water, and dried to give the desired compound as a white powder (25 g).

(d) N-(2,6-difluorophenyl)-1-phenyl-5-n-propyl-1,2,4-triazole-3-sulphonamide

The product of Example A stage (c) (4 g) was added in portions to a stirred solution of 2,6-difluoroaniline (3.6 g) and 4-dimethylaminopyridine (0.2 g) in dry pyridine (25 ml). After 18 hours at 25° C. most of the pyridine was removed in vacuo. The residue was dissolved in 1M sodium hydroxide solution (70 ml) and was extracted with ethyl acetate (2×30 ml). The aqueous layer was acidified with concentrated hydrochloric acid, and the solid was filtered off and recrystallised from toluene to give 3.1 g of the desired product, mp 148°–150° C.

EXAMPLES A2–A102

The following compounds of formula I where $R^4$ represents hydrogen were prepared by methods analogous to those of Example A:

| No | R1 | R2 | R3 (Ph subst:) | m. pt (°C.) |
| --- | --- | --- | --- | --- |
| A2 | Ph | Me | 2,6-diF | 170–172 |
| A3 | Ph | Me | 2,6-diCl, 3-Me | 188–189 |
| A4 | Ph | Et | 2,6-diF | 168–170 |
| A5 | Ph | n-Pr | 2-F | 129–131 |
| A6 | Ph | n-Pr | 3-F | 146–148 |
| A7 | Ph | n-Pr | 2-Cl | 122–124 |
| A8 | Ph | n-Pr | 2,3-diF | 122–124 |
| A9 | Ph | n-Pr | 2,4-diF | 138–140 |
| A10 | Ph | n-Pr | 2,6-diMe | 174–175 |
| A11 | Ph | n-Pr | 2-Cl,6-Me | 173–174 |

| No | R1 | R2 | R3 (Ph subst:) | m. pt (°C.) |
|---|---|---|---|---|
| A12 | Ph | n-Pr | 3-Cl,2-Me | 138–140 |
| A13 | Ph | n-Pr | 2,6-diCl, 3-Me | 189–192 |
| A14 | Ph | n-Pr | 2,3,5,6-tetra F | 118–119 |
| A15 | Ph | i-Pr | 2,5-diF | 136–137 |
| A16 | Ph | i-Pr | 2,6-diF | 157–158 |
| A17 | Ph | i-Pr | 2,6-diCl | 201–202 |
| A18 | Ph | i-Pr | 2-Cl,6-Me | 189–190 |
| A19 | Ph | i-Pr | 2,6-diCl, 3-Me | 195–196 |
| A20 | Ph | n-Bu | 2-F | 142–143 |
| A21 | Ph | n-Bu | 2,6-diF | 169–170 |
| A22 | Ph | n-Bu | 2-Me,6-NO2 | 136–137 |
| A23 | Ph | n-Bu | 2,6-diCl 3-Me | 167–168 |
| A24 | Ph | i-Bu | 2-F | 137–138 |
| A25 | Ph | i-Bu | 2,6-diF | 155–156 |
| A26 | Ph | t-Bu | 2,6-diF | 210–211 |
| A27 | Ph | t-Bu | 2-Cl,6-Me | 194–195 |
| A28 | Ph | Ph | 2-Cl | 182–185 |
| A29 | Ph | Ph | 2-MeO | 162 |
| A30 | Ph | Ph | 2-COOEt | 113–114 |
| A31 | Ph | Ph | 4-COOEt | 184–186 |
| A32 | Ph | Ph | 2-Cl,6-Me | 185–188 |
| A33 | i-Pr | Me | 2-Me | 164–166 |
| A34 | i-Pr | Me | 2-COOEt | 113–115 |
| A35 | i-Pr | Et | 2-Cl,6-Me | 170–173 |
| A36 | i-Pr | Ph | 2,6-diF | 172–173 |
| A37 | i-Pr | Ph | 2-Cl,6-Me | 185–186 |
| A38 | i-pr | 2-ClPh | 2,6-diF | 216–217 |
| A39 | i-Pr | 2-ClPh | 2-Cl,6-Me | 202–203 |
| A40 | Ph | H | 2,6-diF | 186–188 |
| A41 | Ph | H | 2,6-diCl, 3-Me | 145–147 |
| A42 | Ph | Me | 2-Cl,6-Me | 142–143 |
| A43 | Ph | Me | 2-Cl,6-F | 185–187 |
| A44 | Ph | Et | 2,6-diCl, 3-Me | 190–192 |
| A45 | Ph | Et | 2-Cl,6-Me | 139–141 |
| A46 | Ph | n-Pr | 2-Cl,6-F | 151–153 |
| A47 | Ph | i-Pr | pentaF | 123–124 |
| A48 | Ph | n-Bu | 2-Cl,6-SMe | 157–158 |
| A49 | Ph | n-Bu | 2-OCHF2 | 114–115 |
| A50 | Ph | t-Bu | 2,6-diCl | 194–195 |
| A51 | Ph | CF3 | 2,6-diF | 159–163 |
| A52 | Ph | CF3 | 2,6-diCl | 236–239 |
| A53 | Ph | CH2OMe | 2,6-diF | 130–132 |
| A54 | 2-Pyrimidinyl | Me | 2,6-diF | 209–211 |
| A55 | 2-Pyrimidinyl | Me | 2-Cl,6-Me | 224–226 |
| A56 | 2-Pyrimidinyl | Me | 2-Cl,6-F | 217–219 |
| A57 | 2-Pyrimidinyl | Me | 2-Cl | 145–147 |
| A58 | 2-Pyrimidinyl | Me | 2-Me,6-COOMe | 165–167 |
| A59 | 2-Pyrimidinyl | Me | 2-Cl,6-SMe | 206–208 |
| A60 | 2-Pyrimidinyl | Me | 2,6-diBr | 230–232 |
| A61 | 2 Pyrimidinyl | Me | 2-CF3 | 163–165 |
| A62 | 2-Pyrimidinyl | Et | 2,6-diF | 213–215 |
| A63 | 4,6-Dimethyl-2-pyrimidinyl | Me | 2,6-diF | 228–230 |
| A64 | 4,6-Dimethyl-2-pyrimidinyl | Me | 2-Cl | 124–126 |
| A65 | 4,6-Dimethyl-2-pyrimidinyl | Me | 2-Cl,6-Me | 208–210 |
| A66 | 4-methoxy-2-pyrimidinyl | Me | 2,6-diF | 164–166 |
| A67 | 4-Methyl-2-pyrimidinyl | Me | 2,6-diF | 203–205 |
| A68 | Me | Ph | 2,6-diF | 165–166 |
| A69 | Me | Ph | 2,6-diCl, 3-Me | 92–93 |
| A70 | Me | 2,6-diFPh | 2,6-diF | 197–198 |
| A71 | Me | 2-NO2Ph | 2,6-diF | 195–196 |
| A72 | Me | 2-NO2Ph | 2,6-diCl, 3-Me | 233–234 |
| A73 | Ph | Br | 2,6-diF | 155–157 |
| A74 | i-Pr | Me | 2-Cl,6-Me | 197–198 |
| A75 | i-Pr | n-Pr | 2-Cl,6-Me | 178–179 |
| A76 | i-Pr | n-Pr | 2,6-diCl, 3-Me | 187–188 |
| A77 | Me | n-Bu | 2-OCHF2 | 133–134 |
| A78 | Me | n-Bu | 2,6-diCl, 3-Me | 186–187 |
| A79 | Me | n-Bu | 2,6-diF | 159–160 |
| A80 | PhCH2 | Me | 2,6-diF | 159–162 |
| A81 | H | Me | 2,6-diF | 241–243 |
| A82 | 3-Nitropyridin-2-yl | Me | 2,6-diF | 158–160 |
| A83 | Me | i-Pr | 2-COOEt | 113–115 |
| A84 | Me | i-Pr | 2-CN | 164–166 |
| A85 | Et | i-Pr | 2-Cl,3-Me | 170–173 |
| A86 | Ph | COOMe | 2,6-diF | 160–162 |
| A87 | Ph | MeCOOCH2 | 2,6-diF | 142–144 |
| A88 | Ph | HOCH2 | 2,6-diF | 147–149 |
| A89 | Ph | MeCO | 2,6-diF | 140–141 |
| A90 | H | Me | 2,6-diCl, 3-Me | 229–231 |
| A91 | 4-Methyl-2-pyrimidinyl | Me | 2-Cl,6-Me | 176–178 |
| A92 | 4-MeO—6-Me—2-pyrimidinyl | Me | 2,6-diF | 198–200 |
| A93 | 5-Cl—4-MeO—6-Me 2-pyrimidinyl | Me | 2,6-diF | 194–195 |
| A94 | 4-Methoxy-2-pyrimidinyl | Me | 2,6-diF | 194–195 |
| A95 | 4,6-dimethyl-2-pyrimidinyl | H | 2-Cl,6-F | 232–233 |
| A96 | Ph | MeO | 2,6-diF | 189–190 |
| A97 | Ph | MeO | 2-COOMe, 6-Me | 171–172 |
| A98 | Ph | OH | 2-COOMe, 6-Me | 251–252 |
| A99 | 2-Pyrimidinyl | H | 2-Cl,6-F | 246–248 |
| A100 | Ph | Me | 2-MeO | 155–156 |
| A101 | Ph | OH | 2,6-diF | 239–242 |

The following compound of formula I in which R4 is allyl was also prepared by a method analogous to that of Example A:

| No | R1 | R2 | R3 (Ph subst:) | m. pt (°C.) |
|---|---|---|---|---|
| A102 | Ph | Ph | — | 140–141 |

PREPARATIVE EXAMPLE B

N-(2-bromophenyl)-1-phenyl-5-propyl-1,2,4-triazole-3-sulphonamide (Compound B1)

To a cold solution (0° C.) of the product of stage (c) (2.85 g) in dichloromethane (4 ml) was added with stirring a solution of 2-bromoaniline (1.89 g) in pyridine (12 ml). The reaction mixture was stirred at 0° C. for 30 minutes. The mixture was then stirred at room temperature for a further 4 days. The product was then partitioned between 100 ml water and 100 ml dichloromethane, and the aqueous phase was washed with dichloromethane (100 ml). The organic phases were combined and washed with dilute hydrochloric acid (20%, 100 ml), then water (30 ml), and were dried over magnesium sulphate. On solvent removal, an orange oil was obtained which crystallised on trituration with diethyl ether to give orange crystals (3.7 g). These were recrystallised from ethanol to give 2.5 g of the desired product as white crystals, mp 119°–121° C.

PREPARATIVE EXAMPLE C

N-(2,6-dichloro-3-methylphenyl)-5-methyl-1-(2-pyrimidinyl)-1,2,4-triazole-3-sulphonamide (Compound C1)

A suspension of sodium hydride (8.7 g) in dry tetrahydrofuran (400 ml) was stirred at 25° C., and N-acetyl-2,6-dichloro-3-methylaniline (50.4 g) was added portionwise. After stirring for 15 minutes, 5-methyl-1-(2-pyrimidinyl)-1,2,4-triazole-3-sulphonyl chloride (30 g), prepared by a method analogous to that of Example A was added over 5 minutes. The mixture was stirred at 25° C. for 18 hours and the solvent was removed in vacuo. The residue was treated with 1M sodium hydroxide solution (500 ml) for 5 minutes with stirring, and was then extracted with ethyl acetate (500 ml). The ethyl acetate layer was re-extracted with 1M sodium hydroxide solution (300 ml). The combined aqueous phases were acidified with concentrated hydrochloric acid and the solid was filtered off. Recrystallisation from acetonitrile gave 38 g of the desired product, mp 214°-216° C.

Examples C2-C11

The following compounds of formula I where $R^4$ represents hydrogen were prepared by methods analogous to that of Example C:

| No | R1 | R2 | R3 (Ph subst:) | m. pt (°C.) |
|---|---|---|---|---|
| C2 | Ph | Me | 2-Me,6-NO$_2$ | 193-195 |
| C3 | 2-Pyrimidinyl | Me | 2,6-diCl | 223-225 |
| C4 | 2-Pyrimidinyl | Me | 2-Me,6-NO$_2$ | 191-193 |
| C5 | 4,6-Dimethyl-2-pyrimidinyl | Me | 2,6-diCl | 248-249 |
| C6 | 4,6-Dimethyl-2-pyrimidinyl | Me | 2-Me,6-NO$_2$ | 195-196 |
| C7 | 4,6-dimethoxy-1,3,5-triazin-2-yl | Me | 2,6-diCl | 195-197 |
| C8 | 4-Methyl-2-pyrimidinyl | Me | 2,6-diCl | 201-202 |
| C9 | 4-Methyl-2-pyrimidinyl | Me | 2-Me,6-NO$_2$ | 183-184 |
| C10 | 4-Methyl-2-pyrimidinyl | Me | 2,6-diCl,3-Me | 204-205 |

The following compound of formula I where $R^4$ represents hydrogen was also prepared by a method analogous to that of Example C:

| No | R1 | R2 | R3 | m. pt (°C.) |
|---|---|---|---|---|
| C11 | Ph | Me | 3-nitropyrimidin-2-yl | 175-176 |

PREPARATIVE EXAMPLE D 2,6-Dichloro-N,N-bis(1-phenyl-5-n-propyl-1,2,4-triazole-3-sulphonyl)aniline (Compound D1)

The product of Example A stage (c) (4 g) was added to a stirred solution of 2,6-dichloroaniline (2.3 g) in pyridine (20 ml) and the mixture was stirred at 25° C. for 48 hours. The reaction mixture was poured into water (200 ml) and crystallised. The product was recrystallised from ethyl acetate to give 3.35 g of the desired product, mp 262°-264° C.

EXAMPLE D2

The compound corresponding to that of Example D except that $R^3$ represents 2,3,4,5,6-pentafluorophenyl was prepared by a method analogous to that of Example D, mp 139°-140° C.

PREPARATIVE EXAMPLE E

N-(2,6-dichlorophenyl)-5-ethyl-1-phenyl-1,2,4-triazole-3-sulphonamide (Compound E1)

5-Ethyl-1-phenyl-1,2,4-triazole-3-sulphonyl chloride (2.7 g), prepared by a method analogous to that of Example A, was added to a stirred solution of 2,6-dichloroaniline (1.8 g), and 4-dimethylaminopyridine (0.1 g) in dry pyridine (15 ml). After 48 hours at 25° C. most of the pyridine was removed in vacuo, and the residue was dissolved in dichloromethane. The solution was extracted with dilute hydrochloric acid and then re-evaporated. The residue was treated with 4M sodium hydroxide solution (25 ml) at 80° C. for 1 hour and then filtered. The filtered solid was washed with warm water, the filtrate was acidified with concentrated hydrochloric acid, and the product was recrystallised from ethanol to give 1.2 g of desired product, mp 185°-187° C.

Examples E2-E7

The following compounds of formula I in which $R^4$ is hydrogen were prepared by methods analogous to that of Example E:

| No | R1 | R2 | R3 (Ph subst:) | m. pt (°C.) |
|---|---|---|---|---|
| E2 | Ph | Me | 2,6-diCl | 200-201 |
| E3 | Ph | n-Pr | 2,6-diBr | 194-196 |
| E4 | Ph | H | 2,6-diCl | 185-187 |
| E5 | Ph | n-Pr | 2,6-diCl | 192-194 |
| E6 | Ph | n-Pr | 2-Me,6-NO$_2$ | 151-153 |
| E7 | Ph | n-Pr | 2,3-diMe,6-NO$_2$ | 147-149 |

PREPARATIVE EXAMPLE F

N-(2,6-difluorophenyl)-1-(4,6-dimethyl-2-pyrimidinyl)-5-methyl-1,2,4-triazole-3-sulphonamide (Compound F1)

N-(2,6-difluorophenyl)-5-methyl-1,2,4-triazole-3-sulphonamide (5 g) (Compound A81) was added in portions to a suspension of sodium hydride (1.37 g in 80% suspension in oil) in dry dimethylformamide (40 ml). The mixture was stirred for 30 minutes at 25° C., 4,6-dimethyl-2-chloropyrimidine (2.6 g) was added, and the mixture was then stirred at 100° C. for 18 hours. The cooled reaction mixture was poured into water, acidified with glacial acetic acid and then extracted with dichloromethane (3×100 ml). The organic phases were dried and evaporated, and the residue was chromatographed (silica/dichloromethane). The product was recrystallised from ethanol to give 0.8 g of the desired product, mp 228°-230° C., identical to that of Example A63.

EXAMPLES F2-F20

The following compounds of formula I in which $R^2$ is methyl, $R^3$ is 2,6-difluorophenyl and $R^4$ is hydrogen were prepared by methods analogous to that of Example F:

| No | R1 | m. pt (°C.) |
|---|---|---|
| F2 | 2-chloropyrimidin-4-yl | 183-185 |
| F3 | 3-ethyl-1,2,4-thiadiazol-5-yl | 180-181 |
| F4 | pyrazinyl | 201-203 |

-continued

| No | R1 | m. pt (°C.) |
|---|---|---|
| F5 | 4-(2-hydroxyethyl)-6-morpholino-1,3,5-triazin-2-yl | 176–178 |
| F6 | 5-nitropyridin-2-yl | 201–203 |
| F7 | 2,4-dinitrophenyl | 171–173 |
| F8 | 7-chloroquinoxalin-2-yl | 192–195 |
| F9 | 4-methanesulphonylphenyl | 215–217 |
| F10 | 3-phenyl-1,2,4-thiadiazol-5-yl | 244–246 |
| F11 | benzoxazol-2-yl | 210–212 |

The following compound of formula I in which $R^2$ is methyl, $R^3$ is 2,6-dichlorophenyl and $R^4$ is hydrogen was also prepared by a method analogous to that of Example F:

| No | R1 | m. pt (°C.) |
|---|---|---|
| F12 | benzoxazol-2-yl | 212–214 |

The following compounds of formula I in which $R^2$ and $R^4$ are hydrogen and $R^3$ is 2-chloro-6-methylphenyl were also prepared by a method analogous to that of Example F:

| No | R1 | m. pt (°C.) |
|---|---|---|
| F13 | 2,6-dimethoxybenzoyl | 204–207 |
| F14 | thien-2-ylcarbonyl | 233–234 |
| F15 | N—isopropyl-N—(4-methylphenyl)-carbamoyl | 193–194 |
| F16 | N—isopropyl-N—(4-isopropylphenyl)-carbamoyl | 165–166 |
| F17 | N—isopropyl-N—(4-chlorophenyl)-carbamoyl | 181–183 |
| F18 | N—methyl-N—phenylcarbamoyl | 184–186 |
| F19 | 2,2-dimethylpropanoylmethyl | 177–179 |

The following compound of formula I in which $R^2$ and $R^4$ are hydrogen and $R^3$ is 2-ethoxycarbonylphenyl was also prepared by a method analogous to that of Example F:

| No | R1 | m. pt (°C.) |
|---|---|---|
| F20 | N,N—di-isopropylcarbamoyl | 88.5–90 |

PREPARATIVE EXAMPLE G

N-Benzoyl-N-(2,6-difluorophenyl)-5-methyl-1-(2-pyrimidinyl)-1,2,4-triazole-3-sulphonamide (Compound G1)

A suspension of N-(2,6-difluorophenyl)-5-methyl-1-(2-pyrimidinyl)-1,2,4-triazole-3-sulphonamide (1.5 g) (Compound A54) and anhydrous potassium carbonate (0.59 g) in dry acetone (50 ml) was heated under reflux for 30 minutes. A solution of benzoyl chloride (0.6 g) in acetone (50 ml) was added, and the mixture was refluxed for a further 2 hours. The mixture was then allowed to stand at 25° C. for 18 hours, after which it was warmed, filtered and evaporated. The solid produced was recrystallised from acetonitrile to give 1.05 g of the desired product, mp 218°–221° C.

EXAMPLES G2-G7

The following compounds of formula I in which $R^1$ is 2-pyrimidinyl, $R^2$ is methyl and $R^3$ is 2,6-difluorophenyl were prepared by methods analogous to that of Example G:

| Ex | R4 | m. pt (°C.) |
|---|---|---|
| G2 | Me | 193–195 |
| G3 | MeCO | 195–197 |
| G4 | PhCH$_2$ | 158–160 |
| G5 | allyl | 140–142 |
| G6 | MeSO$_2$O | 203–205 |
| G7 | COOMe | 172–174 |

EXAMPLES H1-H23

The following compounds of formula I where $R^4$ represents hydrogen were prepared by methods analogous to that of Example A:

| Ex | R1 | R2 | R3 | mp (°C.) |
|---|---|---|---|---|
| H1 | Ph | Me | thiazol-2-yl | 221–222 |
| H2 | Ph | Me | benzothiazol-2-yl | 266–267 |
| H3 | Ph | Me | 6-methoxyquinolin-8-yl | 146–147 |
| H4 | Ph | Me | 5-methylisoxazol-3-yl | 181–182 |
| H5 | Ph | n-Pr | piperidino | 106–108 |
| H6 | Ph | n-Pr | 3-methylpyridin-2-yl | 160–162 |
| H7 | Ph | n-Bu | 4H—1,2,4-triazol-4-yl | 175–176 |
| H8 | Ph | n-Bu | isoquinolin-5-yl | 259–260 |
| H9 | Ph | Me | 4,6-dimethyl-2-pyrimidinyl | 192–193 |
| H10 | Ph | Me | 6-methoxyquinolin-8-yl | 146–147 |
| H11 | Ph | Me | 5-methylisoxazol-3-yl | 181–182 |
| H12 | Ph | n-Bu | 1,2,4-triazol-4-yl | 175–176 |
| H13 | Ph | Me | 5-methyl-1,3,4-thiadiazol-2-yl | 235–236 |
| H14 | Ph | Me | 4-methylthiazolyl | 218–219 |
| H15 | Ph | Me | 4,5-dimethylthiazolyl | 280–282 |
| H16 | Ph | Me | 6-nitroquinolin-5-yl | 180–181 |
| H17 | Ph | Me | 4-cyano-3-methylthioiso-thiazol-5-yl | 184–185 |
| H18 | Ph | Me | 5-methylthio-1,2,4-triazol-3-yl | 152–153 |
| H19 | Ph | Me | 5-(3-chlorophenyl)-1-methyl-1,2,4-triazol-3-yl | 224–225 |
| H20 | Ph | Me | quinolin-5-yl | 188–189 |
| H21 | Ph | Me | 5-methyl-1-phenyl-1,2,4-triazol-3-yl | 227–228 |
| H22 | Ph | Me | 5-ethyl-1-phenyl-1,2,4-triazol-3-yl | 173–174 |
| H23 | Ph | Me | 1,2,4-triazol-4-yl | >320 |

PREPARATIVE EXAMPLE I

N-(2,6-dichlorophenyl)-1-(4,6-dimethylpyrimidin-2-yl)-1,2,4-triazole-3-sulphonamide N-(2,6-dichlorophenyl)-1,2,4-triazole-3-sulphonamide (2.051 g) was heated for 1 hour at 125° C. with 1.82 g of 2-p-toluenesulphonyl-4,6-dimethylpyrimidine in the presence of 1,8-diazabicyclo(5,4,0)undec-7-ene (2.128 g) in dimethylformamide (35 ml). After distillation of the solvent, the residue was poured into a mixture of water (80 ml) and 1N hydrochloric acid (20 ml), and was then filtered off. This crude product was chromatographed on silica gel using methylene chloride/methanol (95/5) as eluent, to give 2.2 g of the desired product, mp 274°–275° C.

EXAMPLES I2-I46

The following compounds of formula I in which $R^2$ and $R^4$ are both hydrogen and $R^1$ is pyrimidin-2-yl or pyrimidin-2-yl which is further substituted as indicated were prepared by methods analogous to those of Examples A and/or I:

| No | R1 subst: | R3 (Ph subst:) | m. pt (°C.) |
|---|---|---|---|
| I2 | 4,6-diMe | 2,6-diCl,3-Me | 255–256 |
| I3 | — | 2-Cl,6-Me | 204–205 |

-continued

| No | R1 subst: | R3 (Ph subst:) | m. pt (°C.) |
|---|---|---|---|
| I4 | 4,6-diMe | 2-Cl,6-Me | 261–262 |
| I5 | — | 2,6-diF | 231–232 |
| I6 | 4,6-diMe | 2,6-diF | 208–209 |
| I7 | — | 2-$CF_3$ | 196 |
| I8 | 4,6-diMe | 2-$CF_3$ | 227 |
| I9 | 4,6-diMe | 2-COOEt,6-Me | 154–156 |
| I10 | — | 2-COOEt,6-Me | 189 |
| I11 | — | 2,6-diCl | 265–266 |
| I12 | 4-Me | 2,6-diCl | 190 |
| I13 | 4-Me | 2-$CF_3$ | 174–175 |
| I14 | — | 2-COOMe,6-Me | 198–200 |
| I15 | 4,6-diMe | 2-COOMe,6-Me | 187 |
| I16 | 4-Me | 2,6-diF | 199–201 |
| I17 | — | 2,6-diCl,3-Me | 196–198 |
| I18 | 4-Me | 2,6-diCl,3-Me | 201–203 |
| I19 | — | 2-Cl | 179–180 |
| I20 | 4,6-diMe | 2-Cl | 198–199 |
| I21 | — | 2-Me,6-$NO_2$ | 227–228 |
| I22 | 4,6-diMe | 2-Me,6-$NO_2$ | 221–222 |
| I23 | 4,6-diMeO | 2,6-diCl | 255–260 |
| I24 | 4,6-diMeO | 2,6-diF | 205–208 |
| I25 | 4,6-diMeO | 2-COOMe,6-Me | 144–145 |
| I26 | 4,6-diMeO | 2-COOEt,6-Me | 161 |
| I27 | 4-MeO | 2-COOEt,6-Me | 144–145 |
| I28 | 4-MeO | 2-Me,6-$NO_2$ | 196–197 |
| I29 | 4-MeO | 2-Cl,6-Me | 188–189 |
| I30 | 4-MeO | 2,6-diF | 204–205 |
| I31 | 4-Me | 2-Cl,6-Me | 178–179 |
| I32 | 4-Me | 2-Cl | 124–125 |
| I33 | 4-Me | 2-Me,6-$NO_2$ | 176 |
| I34 | 4-Me,6-MeO | 2-$CF_3$ | 222–223 |
| I35 | 4,6-diMe | 4-Br,2,6-diCl | 106–108 |
| I36 | 4-MeO,6-Me | 2,6-diCl | 234–242 |
| I37 | 4-Cl,6-Me | 2,6-diF | 182–183 |
| I38 | 4,6-diMeO | 2-$CF_3$ | 168–169 |
| I39 | 4,6-diMeO | 2,6-diCl,3-Me | 249–250 |
| I40 | 4,6-diMeO | 2-Cl,6-Me | 253–254 |
| I41 | 4,6-diMeO | 2-Me,6-$NO_2$ | 196–197 |

The following compounds of formula I in which $R^2$ and $R^4$ are both hydrogen and $R^1$ is pyrimidin-2-yl or pyrimidin-2-yl which is further substituted as indicated were also prepared by methods analogous to those of Examples A and/or I:

| No | R1 subst: | R3 | m. pt (°C.) |
|---|---|---|---|
| I42 | 4,6-diMe | naphth-1-yl | 249–250 |
| I43 | — | naphth-1-yl | 174–175 |
| I44 | 4-Me | naphth-1-yl | 184–185 |
| I45 | 4,6-diMeO | naphth-1-yl | 211–212 |

The following compound of formula I in which $R^2$ and $R^4$ are both hydrogen and $R^1$ is 4,6-bismethylthio-1,3,5-triazin-2-yl was also prepared by a method analogous to that of Example A and/or I:

| No. | R3 (Ph subst:) | m. pt (°C.) |
|---|---|---|
| I46 | 2,6-diF | 254–256 |

PREPARATIVE EXAMPLE J1

N-(2,6-dichlorophenyl)-1-acetyl-5-amino-1,2,4-triazole-3-sulphonamide (a) 5-Amino-3-benzylthio-1,2,4-triazole 3-Amino-5-mercapto-1,2,4-triazole (40.36 g) was treated at room temperature with sodium hydroxide (13.9 g) in ethanol (450 ml), and benzyl chloride (44.3 g) was added. The mixture was stirred overnight, and was then filtered. The ethanol was evaporated off, and the residue was recrystallised from ethyl acetate to give 64.97 g of the desired product, mp 104° C.

(b) 1-Acetyl-5-amino-3-benzylthio-1,2,4-triazole

Acetyl chloride (12.57 g) in methylene chloride (30 ml) was added to the product of stage (a) (30 g) and triethylamine (25 ml) in methylene chloride (300 ml) at 0° C., and the mixture was stirred at room temperature for 30 minutes. It was then treated with 1N sodium hydroxide (160 ml) and extracted with methylene chloride. The product, after drying, was recrystallised from ethyl acetate to give 33 g of the desired product, mp 146° C.

(c) 1-Acetyl-5-amino-1,2,4-triazole-3-sulphonyl chloride

The product of stage (b) (112 g) was suspended in 1 litre of a mixture of water and glacial acetic acid (1:1), and chlorine was passed in at a temperature of −10° C. over a period of 2 hours, keeping the temperature below 0° C. The product was washed with a minimum of water and pentane, and dried to give 74.5 g of the desired product, mp 166°–168° C.

(d) N-(2,6-dichlorophenyl)-1-acetyl-5-amino-1,2,4-triazole-3-sulphonamide pyridinium salt The product of stage (c) (54 g) was treated with 2,6-dichloroaniline (42.63 g) in pyridine (350 ml) and was stirred at 60° C. for 12 hours. After cooling, the product was filtered off, washed with a little pyridine and ether, and was dried in vacuum to give 53.6 g of the desired product, mp 213°–215° C.

PREPARATIVE EXAMPLE J2

N-(2,6-dichlorophenyl)-5-amino-1,2,4-triazole-3-sulphonamide

The product of Example J1 (53.6 g) was mixed with 2N sodium hydroxide solution (200 ml), and was stirred at room temperature for 10 minutes. With ice-cooling, the pH was reduced to 5 with 2N hydrochloric acid. The product was filtered off, washed with a little water and ether, and dried in vacuum to give 35.4 g of the desired product, mp 265°–267° C.

PREPARATIVE EXAMPLE J3

N-(2,6-dichlorophenyl)-5-methylamino-1,2,4-triazole-3-sulphonamide (a) 1-Acetyl-3-benzylthio-5-methylamino-1,2,4-triazole 3-Benzylthio-5-methylamino-1,2,4-triazole (11.2 g) was dissolved in tetrahydrofuran (70 ml) and triethylamine (5.7 g) was added. Acetyl chloride (4 ml) in tetrahydrofuran (20 ml) was added, and the mixture was stirred at room temperature for 5 hours. The triethylamine hydrochloride was filtered off, and the filtrate was concentrated to give 13.4 g of the desired crude product.

(b) 1-Acetyl-5-methylamino-1,2,4-triazole-3-sulphonyl chloride

The product of stage (a) (13.4 g) was dissolved in glacial acetic acid (50 ml), and water (50 ml) was added. Chlorine was passed through this mixture at −10° C. for 30 minutes, after which the product was filtered off, washed with a little water, and dried in vacuo to give 4.45 g of the desired product.

(c) N-(2,6-dichlorophenyl)-5-methylamino-1,2,4-triazole-3-sulphonamide

The product of stage (b) (4.34 g) was added with stirring to 2,6-dichloroaniline (3.24 g) in pyridine (30 ml), and the mixture was stirred at 50° C. for 18 hours. After removal of the pyridine, the residue was dissolved in sodium hydroxide solution (50 ml) and was extracted with ethyl acetate (50 ml). The aqueous phase was acidified to pH=4-5 with 2N hydrochloric acid, cooled, and the product was filtered off, washed with a little water, and dried to give 3.49 g of the desired product, mp 285°-287° C.

PREPARATIVE EXAMPLE J4

Ethyl 3-(2,6-dichlorophenylsulphamoyl)-5-methylamino-1,2,4-triazole-1-carboxylate The product of Example J3 (2.24 g) was admixed with acetonitrile (100 ml) and potassium carbonate (0.52 g), and ethyl chloroformate (0.8 ml) was added with stirring. The mixture was then refluxed for 5 hours, filtered hot, the filtrate was concentrated, and the residue was triturated with ether. The product was filtered off and dried in vacuo at 70° C. to give 2.65 g of the desired product, mp 202°-203° C.

PREPARATIVE EXAMPLE J5

N-(2,6-dichlorophenyl)-5-(2,5-dimethylpyrrol-1-yl)-1,2,4-triazole-3-sulphonamide The product of Example J2 (6.16 g) was refluxed for 12 hours with hexane-2,5-dione (9.13 g) in ethanol (150 ml) and acetic acid (2 ml). After removal of the solvents and excess diketone, the residue was chromatographed over silica gel with hexane/ethyl acetate to give 2.9 g of the desired product, mp 107°-108° C.

PREPARATIVE EXAMPLE J6

N-(2,3-dichlorophenyl)-5-(2,5-dimethylpyrrol-1-yl)-1,2,4-triazole-3-sulphonamide The product of Example J1(c) (4.49g) was stirred with 2,3-dichloroaniline (3.24 g) in dry pyridine (75 ml) under nitrogen for 5 hours at 70° C. The pyridine was then removed, and the residue was dried under high vacuum. The crude product was then refluxed with ethanol (150 ml), acetic acid (5 ml) and hexane-2,5-dione (9.13 g) for 8 hours, after which the solvents were removed, and the product was chromatographed on silica gel using ethyl acetate/hexane to give 4.4 g of the desired product, mp 185° C.

EXAMPLES J7-J27

The following compounds of formula I in which $R^4$ is hydrogen and $R^2$ is pyrrol-1-yl substituted as indicated were prepared by methods analogous to those of Examples J1-J5:

| No | R1 | R2 subst | R3 (Ph subst:) | m. pt (°C.) |
|---|---|---|---|---|
| J6 | H | 2,5-diMe | 2,3-diCl | 185 |
| J7 | H | 2,5-diMe | 2-Cl,6-Me | 170 |
| J8 | H | 2,5-diMe | 2,6-diCl,3-Me | 196 |
| J9 | H | 2,5-diMe | 2,6-diF | 185-186 |
| J10 | H | 2,5-diMe | 2,6-diMe | 186 |
| J11 | H | 2,5-diMe | 2-CF3 | 189-193 |
| J12 | H | 2,5-diMe | 2-Cl | 184 |
| J12 | H | 2,5-diMe | pentaF | 92 |
| J13 | H | 2,5-diMe | 2-MeO | 84 |
| J14 | H | 2,5-diMe | 2,4-diCl | 153 |
| J15 | H | 2,5-diMe | 2,5-diCl | 208 |
| J16 | H | 2,5-diMe | — | 154 |
| J17 | H | 2,5-diMe | 2-Cl,6-F | 159 |
| J18 | H | 2,5-diMe | 2-F | 144 |
| J19 | H | 2,5-diMe | 2-Cl,5-Me | 211 |
| J20 | H | 2,5-diMe | 2,5-F | 164 |
| J21 | H | — | 2-Cl,6-F | 176 |
| J22 | H | — | 2-CF3 | 70 |
| J23 | H | — | 2,6-diCl | 230 |
| J24 | t-Bu | — | 2,6-diCl | 210 |
| J25 | t-Bu | — | 2,6-diCl,3-Me | 155 |

The following compounds of formula I in which $R^4$ is hydrogen and $R^2$ represents pyrrol-1-yl substituted as indicated were also prepared by methods analogous to those of Examples J1-J5:

| No | R1 | R2 | R3 | m. pt (°C.) |
|---|---|---|---|---|
| J26 | H | 2,5-diMe | 2-COOMe-3-thienyl | 144 |
| J27 | H | 2,5-diMe | 1-naphthyl | 207 |

PREPARATIVE EXAMPLE K1

N-(2,6-difluorophenyl)-5-methylamino-1-phenyl-1,2,4-triazole-3-sulphonamide (a) 3-Benzylthio-5-formylamino-1-phenyl-1,2,4-triazole 5-Amino-3-benzylthio-1-phenyl-1,2,4-triazole (45 g) was suspended in acetic anhydride (31 ml) and formic acid (16.09 ml), and the mixture was stirred for 1 hour at 80° C. The solvents were then removed, and the residue was recrystallised from ethyl acetate to give 35.4 g of the desired product, mp 94° C.

(b) 3-Benzylthio-5-methylamino-1-phenyl-1,2,4-triazole

The product of stage (a) (31 g) was mixed with dioxan (200 ml) and 96% sodium borohydride (19.6 g) at room temperature, and acetic acid (30 ml) was added with vigorous stirring. The mixture was stirred at 100° C. for 2 hours, after which the solvents were removed and the mixture was added carefully to water. The product was then extracted with ethyl acetate and chromatographed on silica gel to give 21.4 g of the desired product.

(c) 5-Methylamino-1-phenyl-1,2,4-triazole-3-sulphonyl chloride

The product of stage (b) (21 g) was suspended in a mixture of water (50 ml) and acetic acid (50 ml). Chlorine was passed into the mixture at a temperature of from −10° C. to 0° C., and the product was extracted with ethyl acetate. The oily product was chromatographed on silica gel using hexane/ethyl acetate to give 15 g of the desired product.

(d) N-(2,6-difluorophenyl)-5-methylamino-1-phenyl-1,2,4-triazole-3-sulphonamide

The product of stage (c) (3.27 g) was stirred at room temperature for 2 hours, then at 60° C. for 1 hour and then overnight at room temperature with 2,6-difluoroaniline (2.58 g) in pyridine (20 ml), after which the pyridine was removed, and the residue was chromatographed on silica gel using hexane/ethyl acetate.

The product was recrystallised from ethyl acetate to give 3.5 g of the desired product, mp 180°–181° C.

PREPARATIVE EXAMPLE K2

N-(2,6-dichlorophenyl)-5-amino-1-(4,6-dimethylpyrimidin-2-yl)-1,2,4-triazole-3-sulphonamide

(a) 5-Amino-3-benzylthio-1,2,4-triazole

5-Amino-3-mercapto-1,2,4-triazole (40.36 g) in ethanol (450 ml) was treated at room temperature with solid sodium hydroxide (13.9 g), and benzyl chloride (44.3 g) was added dropwise. The solution was stirred overnight, filtered, and the residue was recrystallised from ethyl acetate and dried to give 64.97 g of desired product, mp 104° C.

(b) 1-Acetyl-5-amino-3-benzylthio-1,2,4-triazole

Acetyl chloride (12.57 g) in methylene chloride (30 ml) was added to the product of stage (a) (30 g) in triethylamine (25 ml) and methylene chloride (300 ml) at 0° C., and the mixture was stirred for 30 minutes. Then 1N sodium hydroxide was added, and the solution was extracted with methylene chloride. On drying, and recrystallisation from ethyl acetate, 33 g of the desired product, mp 146° C., were obtained.

(c) 1-Acetyl-5-amino-1,2,4-triazole-3-sulphonyl chloride

The product of stage (b) (112 g) was suspended in a 1:1 mixture of water and acetic acid and chlorine was passed through this suspension at a temperature of −10° C. over 2 hours. The product was filtered off, washed with a little water and pentane, and then dried to give 74.5 g of the desired product, mp 166°–168° C.

(d) 1-Acetyl-N-(2,6-dichlorophenyl)-5-amino-1,2,4-triazole-3-sulphonamide pyridinium salt The product of stage (c) (54 g) was treated with 2,6-dichloroaniline (42.63 g) in pyridine (350 ml), and the mixture was stirred at 60° C. for 12 hours. After cooling, the product was filtered off, washed with a little pyridine and ether, and dried in vacuo to give 53.6 g of the desired product, mp 213°–215° C.

(e) N-(2,6-dichlorophenyl)-5-Amino-1,2,4-triazole-3-sulphonamide

The product of stage (d) (53.6 g) was dissolved in 2N sodium hydroxide (200 ml), and was stirred at room temperature for 10 minutes. The solution was then taken to pH=5 with 2N hydrochloric acid, and the product was filtered off, washed with a little water and ether, and then dried in vacuo to give 35.4 g of the desired product, mp 265°–267° C.

(f) N-(2,6-dichlorophenyl)-5-amino-1-(4,6-dimethylpyrimidin-2-yl)-1,2,4-triazole-3-sulphonamide The product of stage (e) (2.15 g) was stirred in dimethylformamide (35 ml) and 2-p-tosyl-4,6-dimethylpyrimidine (1.82 g) for 4 hours at 120° C. in the presence of 1,8-diazabicyclo(5,4,0)undec-7-ene (2.128 g). After removal of the solvents, the residue was stirred in 1N hydrochloric acid (100 ml) and the product was filtered off. This was then chromatographed on silica gel using methylene chloride/methanol (95:5) to give 2.1 g of the desired product, mp 306°–312° C.

EXAMPLES K3–K72

The following compounds of formula I in which $R^4$ is hydrogen were prepared by methods analogous to those of Examples K1 and K2:

| No | R1 | R2 | R3 (Ph subst:) | m. pt (°C.) |
|---|---|---|---|---|
| K3 | Ph | $NH_2$ | 2,6-diCl | >260 |
| K4 | Ph | $NH_2$ | 2-Cl,6-F | 257 |
| K5 | Ph | $NH_2$ | 2,6-diCl, 3-Me | 248 |
| K6 | Ph | $NH_2$ | 2-Cl,6-Me | 226 |
| K7 | Ph | $NH_2$ | 2,6-diF | 218 |
| K8 | 4-MePh | $NH_2$ | 2-Cl,6-F | 232 |
| K9 | 4-MePh | $NH_2$ | 2,6-diCl, 3-Me | 236 |
| K10 | 4-MePh | $NH_2$ | 2,6-diF | 240 |
| K11 | 4-MePh | $NH_2$ | 2,6-diCl | 260 |
| K12 | 2-MePh | $NH_2$ | 2,6-diF | 194 |
| K13 | 2-MePh | $NH_2$ | 2,6-diCl | 155 |
| K14 | Ph | NHEt | 2,6-diCl, 3-Me | 176 |
| K15 | Ph | NHEt | 2,6-diCl | 168 |
| K16 | Ph | NHEt | 2,6-diF | 135–137 |
| K17 | Ph | NHMe | 2,6-diCl, 3-Me | 125–127 |
| K18 | Ph | NHMe | 2,6-diCl | 132–134 |
| K19 | Ph | N(CHO)Me | 2,6-diF | 176–177 |
| K20 | Ph | Pyrrol-1-yl | 2,6-diCl | 208–209 |
| K21 | Ph | Pyrrol-1-yl | 2,6-diF | 157–158 |
| K22 | Ph | Pyrrol-1-yl | 2-Cl,6-F | 190–191 |
| K23 | Ph | N=CHOMe | 2,6-diCl | 196 |
| K24 | Ph | N=CHOEt | 2,6-diCl | 145–146 |
| K25 | 3,5-diMePh | $NH_2$ | 2,6-diCl | 233–234 |
| K26 | 3,5-diMePh | $NH_2$ | 2,6-diF | 194–195 |
| K27 | 3,5-diMePh | $NH_2$ | 2,6-diCl, 3-Me | >230 |
| K28 | 3,5-diMePh | NHEt | 2,6-diF | 199–200 |
| K29 | 3,5-diMePh | NHEt | 2,6-diCl, 3-Me | 160–161 |
| K30 | 3,5-diMePh | NHEt | 2,6-diCl | 155–157 |
| K31 | 3,5-diMePh | Pyrrol-1-yl | 2,6-diF | 226–227 |
| K32 | 3,5-diMePh | $NH_2$ | 2-Cl,6-F | 169–170 |
| K33 | 3,5-diMePh | NHEt | 2-Cl,6-F | 169–170 |
| K34 | 4,6-Dimethylpyrimidin-2-yl | $NH_2$ | 2,6-diCl, 3-Me | 309–313 |
| K35 | 4,6-Dimethylpyrimidin-2-yl | $NH_2$ | 2,6-diF | >250 |
| K36 | 4,6-Dimethoxy-1,3,5-triazin-2-yl | $NH_2$ | 2,6-diCl, 3-Me | 236–237 |
| K37 | Pyrimidin-2-yl | $NH_2$ | 2,6-diCl | 286–290 |
| K38 | Pyrimidin-2-yl | $NH_2$ | 2,6-diCl, 3-Me | 250–254 |
| K39 | Pyrimidin-2-yl | $NH_2$ | 2,6-diF | 289–294 |
| K40 | Pyrimidin-2-yl | $NH_2$ | 2-Cl,6-F | 272–280 |
| K41 | Pyrimidin-2-yl | $NH_2$ | 2-Cl,6-Me | 260–264 |
| K42 | 4,6-Dimethylpyrimidin-2-yl | $NH_2$ | 2-$CF_3$ | 250–251 |
| K43 | 4,6-Dimethylpyrimidin-2-yl | $NH_2$ | 2-Cl,6-Me | 272–273 |
| K44 | 4,6-Dimethoxy-1,3,5-triazin-2-yl | $NH_2$ | 2,6-diF | 213–214 |
| K45 | 4,6-Dimethoxy-1,3,5-triazin-2-yl | $NH_2$ | 2-Cl,6-Me | 227–228 |
| K46 | Pyridin-2-yl | $NH_2$ | 2,6-diCl | 280–282 |
| K47 | Pyridin-2-yl | $NH_2$ | 2,6-diMe, 3-Me | 236 |
| K48 | Pyridin-2-yl | $NH_2$ | 2,6-diBr | 279–282 |
| K49 | Pyridin-2-yl | $NH_2$ | 2-Cl,6-F | 254–262 |
| K50 | Pyridin-2-yl | $NH_2$ | 2-Cl,6-Me | 246–253 |
| K51 | Pyridin-2-yl | $NH_2$ | 2-$CF_3$ | 231–236 |
| K52 | Pyrimidin-2-yl | pyrrol-1-yl | 2-Cl,6-Me | 169 |
| K53 | Pyrimidin-2-yl | $NH_2$ | 2-$CF_3$ | 218–219 |
| K54 | 4-Methylpyrimidin-2-yl | $NH_2$ | 2,6-diCl, 3-Me | 264 |
| K55 | 4-Methylpyrimidin-2-yl | $NH_2$ | 2,6-diCl | 295 |
| K56 | 4-Methylpyrimidin-2-yl | $NH_2$ | 2,6-diF | 270–275 |
| K57 | 4,6-Dimethoxy- | $NH_2$ | 2,6-diCl | 246–249 |

-continued

| No | R1 | R2 | R3 (Ph subst:) | m. pt (°C.) |
|---|---|---|---|---|
|  | pyrimidin-2-yl |  |  |  |
| K58 | 4,6-Dimethoxy-pyrimidin-2-yl | NH$_2$ | 2,6-diF | 248 |
| K59 | 4,6-dimethyl-pyrimidin-2-yl | MeNH | 2,6-diF | 268–270 |
| K60 | 4,6-dimethyl-pyrimidin-2-yl | MeNH | 2,6-diCl | 243–245 |
| K61 | 4,6-dimethoxy-pyrimidin-2-yl | MeNH | 2,6-diF | 221–222 |
| K62 | 4,6-dimethoxy-pyrimidin-2-yl | MeNH | 2,6-diCl | 221–223 |
| K63 | 4,6-dimethyl-pyrimidin-2-yl | EtNH | 2,6-diCl | 242–243 |
| K64 | 4,6-dimethyl-pyrimidin-2-yl | EtNH | 2,6-diF | 223–224 |
| K65 | 4,6-dimethoxy-pyrimidin-2-yl | NH$_2$ | 2,6-diCl, 3-Me | 277–288 |
| K66 | 4,6-dimethoxy-pyrimidin-2-yl | NH$_2$ | 2-CF$_3$ | 237–238 |
| K67 | pyrimidin-2-yl | NH$_2$ | 2-CF$_3$ | 230–231 |
| K68 | pyridin-2-yl | NH$_2$ | 2,6-diF | 289–291 |
| K69 | pyrimidin-2-yl | NH$_2$ | 2,6-diBr | 292–298 |
| K70 | pyrimidin-2-yl | pyrrol-1-yl | 2,6-diF | 148–156 |

The following compounds of formula I in which R$^4$ is hydrogen were also prepared by methods analogous to those of Examples K1 and K2:

| No | R1 | R2 | R3 | m. pt (°C.) |
|---|---|---|---|---|
| K71 | 4,6-Dimethylpyrimidin-2-yl | NH$_2$ | naphth-1-yl | 287–288 |
| K72 | Pyrimidin-2-yl | NH$_2$ | naphth-1-yl | 242–243 |

INTERMEDIATES PREPARATION

The following Examples are of various intermediates in the preparation of compounds of formula I. Intermediates Preparation Example 1 is an alternative method for the preparation of a compound of formula II from a compound of formula III, which may be used instead of the process of Preparative Example A stage (c). The other Intermediates Preparation Examples are of the interconversion of compounds of formula III to give appropriately substituted starting materials for the processes of Example A stage (c), Intermediates Preparation Example 1, or processes analogous to these.

INTERMEDIATES PREPARATION 1

1-(4,6-Dimethoxy-1,3,5-triazin-2-yl)-5-methyl-1,2,4-triazole-3-sulphonyl chloride A solution of 3-benzylthio-1-(4,6-dimethoxy-1,3,5-triazin-2-yl)-5-methyl-1,2,4-triazole (6 g) in dichloromethane (60 ml) was treated with silica gel (14 g) 60–120 mesh and water (2.8 g). Sulphuryl chloride (10.6 ml) in dichloromethane (12 ml) was added dropwise with stirring whilst maintaining a temperature of 5° C. for 2 hours. The silica gel was filtered off, washed with dichloromethane (150 ml) and ethyl acetate (100 ml), and the combined washings were extracted with water and aqueous sodium bicarbonate. The organic layer was dried and evaporated at 40° C. in vacuo. The residue was triturated with ether and filtered to give 3 g of the desired product.

Intermediates Preparation 2

3-Benzylthio-5-bromo-1-phenyl-1,2,4-triazole

3-Benzylthio-1-phenyl-1,2,4-triazole (5 g) in dry tetrahydrofuran (50 ml) at −70° C. was treated dropwise with n-butyllithium (1.05 equivs). The solution was stirred at −70° C. for 10 minutes and cyanogen bromide (1.98 g) was added rapidly. The mixture was allowed to warm to room temperature and was then quenched with ethanol. The volatile materials were removed in vacuo, and the crude product was chromatographed on silica using dichloromethane to give 4.3 g of the desired product as a yellow oil.

Intermediates Preparation 3

5-Methanesulphonyl-1-(pyrimidin-2-yl)-1,2,4-triazole-3-sulphonyl chloride (a) 3-Benzylthio-5-methylthio-1,2,4-triazole A solution of sodium hydroxide (16 g) in water (60 ml) was added to a suspension of 3-benzylthio-5-mercapto-1,2,4-triazole (89.2 g) in dichloromethane (400 ml) containing benzyltriethylammonium chloride (1 g) with stirring and cooling to 15°–20° C. To this mixture methyl iodide (56.8 g) was added, and stirring was continued at room temperature for 24 hours. The dichloromethane phase was separated, washed with water twice, dried over magnesium sulphate and run down to give 94 g of crude product, which was recrystallised from toluene to give 80.7 g of desired product, mp 80°–82° C.

(b) 3-Benzylthio-5-methylthio-1-(pyrimidin-2-yl)-1,2,4-triazole

The product of stage (a) (50 g) was treated with 2-chloropyrimidine (24.4 g) in a method analogous to that of Example F, to give, after chromatographic separation of two products, 23.6 g of the desired product.

(c) 5-Methanesulphonyl-1-(pyrimidin-2-yl)-1,2,4-triazole-3-sulphonyl chloride

Chlorine gas was bubbled into a suspension of the product of stage (b) (8 g) in water (45 ml) and acetic acid (45 ml) at −5° to 0° C. with stirring until 9.9 g had been absorbed. Stirring was continued for 10 minutes at −5° to 0° C. prior to filtration. The product was washed in aqueous acetic acid (1:1), water, 40–60 petroleum ether and finally ether. Drying gave 6.3 g of crude product which was recrystallised from ethyl acetate and acetonitrile to give 3.1 g of desired product, mp 214°–217° C.

Intermediates Preparation 4

5-Chloro-1-(pyrimidin-2-yl)-1,2,4-triazole-3-sulphonyl chloride (a) 3,5-bis(benzylthio)-1-(pyrimidin-2-yl)-1,2,4-triazole 3,5-Bis(benzylthio)-1,2,4-triazole (50 g), 2-chloropyrimidine (18.3 g) and potassium carbonate (22.1 g) were heated in dimethylformamide (200 ml) at 100° C. for 12 hours. After addition to ice-water, the product was extracted into dichloromethane (twice). The dichloromethane solution was washed with water (3 times), dried over magnesium sulphate and run down, leaving 64.4 g of crude title. Recrystallisation from methanol gave 39 g of the desired product, mp 86°–88° C.

(b) 5-Chloro-1-(pyrimidin-2-yl)-1,2,4-triazole-3-sulphonyl chloride

Chlorine was bubbled into a suspension of the product of stage (a) (10 g) in water (50 ml) and acetic acid (50 ml) at −5° to 0° C. until 15 g had been absorbed. The mixture was then stirred for 15 minutes at −5° to −10° C. and was filtered. The white precipitate was washed with cold aqueous acetic acid (1:1), water and 40–60 petroleum ether, to give 7.6 g of crude product. This solid was heated under reflux in ethyl acetate (300 ml) for 2 hours 30 minutes. The residual white by-product was filtered off, and the solution was run down in vacuo. The residue was warmed with ether (100 ml), filtered through kieselguhr, and reduced in volume to 10 ml. Cooling in ice produced the desired product as a solid which was filtered off to give 2.2 g, mp 98°–101° C.

Intermediates Preparation 5

3-Benzylthio-5-methoxy-1-phenyl-1,2,4-triazole

3-Benzylthio-5-hydroxy-1-phenyl-1,2,4-triazole (15 g) in dichloromethane (60 ml) was treated with trimethyloxonium tetrafluoroborate (15.7 g) and allowed to stand for 18 hours at room temperature. The reaction mixture was poured into water (200 ml) and the aqueous layer was washed with dichloromethane (2×100 ml). The dried organic layer was evaporated and then purified by column chromatography (silica/petroleum ether:ether), to give 8.1 g of the desired product.

Intermediates Preparation 6

5-Acetoxy-1-phenyl-1,2,4-triazole-3-sulphonyl chloride (a) 1-Ethoxycarbonyl-1-phenythiosemicarbazide A mixture of 1-phenylthiosemicarbazide (25 g), ethanol (180 ml) and ethyl chloroformate (17 ml) was heated under reflux with stirring for 30 minutes. The mixture was cooled to room temperature and the solid was filtered, washed with ethanol and then with ether to give 28.9 g of the desired product.

(b) 5-Hydroxy-1-phenyl-1,2,4-triazol-3-thiol

The product of stage (a) (28.9 g) was treated with a solution of sodium hydroxide (7.5 g) in water (150 ml). The suspension was heated under reflux with stirring for 45 minutes and then cooled to 25° C. The pH of the solution was adjusted to 1.0 with concentrated hydrochloric acid and the resulting solid was filtered and washed with water to give 20.2 g of the desired product.

(c) 3-Benzylthio-5-hydroxy-1-phenyl-1,2,4-triazole

The product of stage (b) (20 g), ethanol (300 ml) and sodium hydroxide (5 g) were stirred together for 10 minutes. Benzyl chloride (12.3 ml) was added, and the mixture was heated under reflux with stirring for 24 hours. The solvent was removed in vacuo, and the residue was treated with water. The pH was adjusted to 1.0 with concentrated hydrochloric acid, and the solid was filtered, washed with water and recrystallises from ethanol to give 21.75 g of the desired product.

(d) 5-Acetoxy-3-benzylthio-1-phenyl-1,2,4-triazole

A mixture of the product of stage (c) (20 g), toluene (150 ml) and acetyl chloride (12.2 ml) was heated under reflux for 5 hours. The volatile materials were removed in vacuo, and the residue was triturated with ether and filtered off. Recrystallisation from ethanol gave 19.8 g of desired product.

(e) 5-Acetoxy-1-phenyl-1,2,4-triazole-3-sulphonyl chloride

A suspension of the product of stage (d) (10 g) in glacial acetic acid (20 ml) and water (30 ml) was stirred at −5° C. Chlorine gas was bubbled through the stirred solution for 40 minutes, and water (200 ml) was then added. The solid was filtered off, washed with water and air-dried to give 6.3 g of the desired product.

On subsequent reaction of this compound with 2.6-difluoroaniline in the manner of Example A, the acetoxy group is hydrolysed in the work-up of the product to give N-(2,6-difluorophenyl)-5-hydroxy-1-phenyl-1,2,4-triazole-3-sulphonamide.

Intermediates Preparation 7

3-Benzylthio-5-bromo-1-phenyl-1,2,4-triazole n-Butyllithium (50 ml) was added dropwise to a stirred solution of 3-benzylthio-1-phenyl-1,2,4-triazole (31.8 g) in dry tetrahydrofuran (200 ml) at −70° C. Bromine (19 g) was added and the reaction mixture was allowed to warm to room temperature and then quenched with water. After washing with brine, the organic phase was dried and evaporated to give a yellow oil. Purification by chromatography over silica with dichloromethane and petroleum ether afforded the desired product as a pale yellow oil.

The corresponding compounds in which the substituent at the 5-position was methoxycarbonyl, acetyl and hydroxymethyl were also prepared by analogous methods using methylchloroformate, N,N-dimethylacetamide and N,N-dimethylformamide respectively as the electrophile followed by reduction using sodium borohydride.

Formulation Example 1

An 80% active acid equivalent water soluble powder concentrate was prepared from the following ingredients:

|  | % w/w |
| --- | --- |
| Compound of Example A54, K$^+$ salt | 94.8 |
| Neosyl (silica) | 2.7 |
| Arkopon T (sodium N—methyltauride) | 2.5 |

Analogous compositions were also made containing 20, 40, and 60% w/w active acid equivalent of the compounds of the other Examples provided hereinbefore.

Formulation Example 2

A 7.5% aqueous solution formulation was prepared from the following ingredients:

|  | g/l |
| --- | --- |
| Compound of Example C1 | 75.0 |
| Potassium hydroxide (85% pellets) | 12.4 |
| N—methylpyrrolidone | 506.7 |

|  | g/l |
|---|---|
| Water | q.s. |

Analogous formulations were also made containing 60 g/l and 75 g/l of the compounds of the other Examples provided hereinbefore, particularly the compound of Example C4.

Formulation Example 3

A 10% aqueous solution was prepared from the following ingredients:

|  | g/l |
|---|---|
| Compound of Example A63 | 100.0 |
| Potassium hydroxide (1M) | 263.1 |
| Water | q.s. |

Analogous formulations were also made containing 5% and 10% of the compounds of the other Examples provided hereinbefore.

HERBICIDAL EXAMPLE A (Pre-Emergence)

Seeds of the weed species listed below were sown in anodised aluminium pans 19 cm long×9.5 cm wide×6 cm deep, containing sterilized sandy loam. They were watered and then sprayed with the compounds of the Examples listed below formulated as a solution/suspension in 1:1 by volume of acetone and the wetting agent polyoxyethylene (20 mols) monolaurate solution (2 g per liter).

The concentration of each test compound and volume of application were calculated to give the desired rate of application of the compound in 450 liters per hectare. After 3 to 4 weeks growth in the controlled environment room (20° C.; 75–95% relative humidity; 14 hours per day artificial illumination) the plants were visually assessed for any herbicidal response.

All differences from an untreated control were scored accordingly to an index where 0=no effect, 1=1–24% effect, 2=25–69% effect, 3=70–89% effect and 4=90–100% effect. In the table below, the following letters are used to denote the plant species:

a—*Polygonum lapathifolium* (Pale persicaria)
b—*Galium aparine* (cleavers)
c—*Chrysanthemum segetum* (corn marigold)
d—*Alopecurus myosuroides* (blackgrass)
e—*Elymus repens* (Couchgrass)
f—*Avena fatua* (wild oat)
g—*Abutilon theophrasti* (velvetleaf)
h—*Cyperus rotundus* (purple nutsedge)
i—*Pharbitis purpurea* (morningglory)
j—*Echinochloa crus-galli* (barnyardgrass)
k—*Setaria viridis* (green foxtail)
l—*Solanum nigrum* (black nightshade)

The results obtained were as follows:

| Ex | Kg/ha | a | b | c | d | e | f | g | h | i | j | k | l |
|---|---|---|---|---|---|---|---|---|---|---|---|---|---|
| A2 | 1.0 | 4 | 4 | 4 | 3 | 2 | 0 | 4 | 4 | 4 | 3 | 2 | 4 |
| A3 | 1.0 | 0 | 4 | 4 | 0 | 0 | 0 | 2 | 0 | 0 | 0 | 3 | 4 |
| A4 | 1.0 | 2 | 3 | 3 | 0 | 0 | 0 | 2 | 1 | 1 | 2 | 1 | 3 |
| A6 | 1.0 | 2 | 2 | 3 | 0 | 0 | 0 | 0 | 0 | 0 | 2 | 2 | 4 |
| A9 | 1.0 | 2 | 2 | 0 | 2 | 0 | 0 | 0 | 0 | 0 | 0 | 2 | 4 |
| A18 | 1.0 | 2 | 0 | 0 | 2 | 0 | 2 | 0 | 0 | 0 | 1 | 4 | 4 |
| A19 | 1.0 | 3 | 3 | 4 | 0 | 0 | 2 | 0 | 0 | 0 | 2 | 0 | 0 |
| A25 | 2.5 |   | 4 | 3 | 2 | 2 | 2 | 0 | 0 | 0 | 2 | 0 | 0 |
| A43 | 1.0 | 4 | 4 | 4 | 2 | 0 | 1 | 4 | 3 | 3 | 0 | 0 | 4 |
| A44 | 1.0 | 0 | 4 | 4 | 0 | 2 | 0 | 2 | 0 | 0 | 0 | 0 | 2 |
| A53 | 1.0 | 4 | 4 | 4 | 2 | 0 | 0 | 3 | 4 | 0 | 2 | 4 | — |
| A54 | 1.0 | 4 | 4 | 4 | 3 | 4 | 1 | 4 | 4 | 4 | 3 | 2 | — |
| A55 | 1.0 | 4 | 4 | 4 | 2 | 2 | 0 | 4 | 4 | 3 | 4 | 4 |   |
| A56 | 1.0 | 4 | 4 | 4 | 2 | 2 | 2 | 4 | — | 4 | 3 | 3 | — |
| A57 | 0.5 | 2 | 2 | 4 | 1 | 0 | 0 | 2 | 3 | 3 | 0 | 0 | 4 |
| A63 | 0.5 | 4 | 4 | 4 | 4 | 4 | 4 | 0 | 0 | 0 | 0 | 0 | 3 |
| A65 | 0.5 | 3 | 4 | 4 | 4 | 4 | 3 | 4 | 4 | 4 | 4 | 4 | 4 |
| B1 | 2.5 | 4 | 4 | 4 | 2 | 2 | 0 | 2 |   | 2 | 2 | 0 | 4 |
| C1 | 1.0 | 4 | 4 | 4 | 2 | 2 | 0 | 4 | 4 | 4 | 2 | 0 | — |
| C2 | 1.0 | 4 | 4 | 4 | 0 | 2 | 0 | 4 | 4 | 2 | 2 | 0 | — |
| C3 | 1.0 | 4 | 4 | 4 | 2 | 2 | 0 | 4 | 4 | 2 | 2 | — |   |
| C4 | 1.0 | 4 | 4 | 4 | 3 | 2 | 2 | 4 | — | 4 | 3 | 4 | 4 |
| C5 | 0.5 | 4 | 4 | 4 | 4 | 4 | 3 | 4 | 4 | 4 | 4 | 4 | 4 |
| C6 | 0.5 | 3 | 4 | 4 | 3 | 4 | 3 | 4 | 4 | 4 | 4 | 4 | 4 |
| E2 | 1.0 | 4 | 4 | 4 | 0 | 0 | 0 | 2 | 0 | 0 | 0 | 0 | 4 |
| E3 | 1.0 | 2 | 4 | 4 | 0 | 0 | 0 | 1 | 0 | 0 | 0 | 0 | 2 |
| E4 | 1.0 | 2 | 4 | 4 | 0 | 0 | 0 | 2 | 2 | 2 | 0 | 0 | 3 |

HERBICIDAL EXAMPLE B (Post-Emergence)

Seeds of the plant species listed below were sown in anodised aluminium pans, 19 cm long×9.5 cm×6 cm deep, containing sterilised sandy loam. They were watered and then placed in a controlled environment room (20° C.; 75–95% relative humidity; 14 hours per day artificial illumination). Fourteen or twenty one days after sowing (depending on the species but when most plants had 2 to 3 true leaves) the seedlings received a foliar spray of the compounds of the Examples listed below, formulated as a solution/suspension in 1:1 by volume of acetone and the wetting agent polyoxyethylene (20 mols) monolaurate solution (2 g per liter).

The concentration of each test compound was calculated to give the desired rate of application of the compound in 450 liters per hectare. After 2 to 3 weeks growth in the controlled environment room the plants were visually assessed for any herbicidal response.

All differences from an untreated control were scored according to an index where 0=no effect, 1=1–24% effect, 2=25–69% effect, 3=70–89% effect and 4=90–100% effect. In the table below, the following letters are used to denote the plant species:

a—*Polygonum lapathifolium* (Pale persicaria)
b—*Galium aparine* (cleavers)
c—*Chrysanthemum segetum* (corn marigold)
d—*Alopecurus myosuroides* (blackgrass)
e—*Elymus repens* (Couchgrass)
f—*Avena fatua* (wild oat)
g—*Abutilon theophrasti* (velvetleaf)
h—*Cyperus rotundus* (purple nutsedge)
i—*Pharbitis purpurea* (morningglory)
j—*Echinochloa crus-galli* (barnyardgrass)
k—*Setaria viridis* (green foxtail)
l—*Solanum nigrum* (black nightshade)

The results obtained were as follows:

| Ex | Kg/ha | a | b | c | d | e | f | g | h | i | j | k | l |
|---|---|---|---|---|---|---|---|---|---|---|---|---|---|
| A2 | 1.0 | 3 | 4 | 4 | 2 | 0 | 2 | 4 | 1 | 2 | 2 | 0 | 3 |
| A4 | 1.0 | 2 | 3 | 3 | 0 | 0 | 0 | 2 | 1 | 1 | 2 | 1 | 3 |
| A43 | 1.0 | 2 | 3 | 3 | 2 | 0 | 0 | 3 | 0 | 2 | 2 | 1 | 4 |
| A53 | 1.0 | 1 | 4 | 2 | 2 | 0 | 1 | 1 | 1 | 2 | 3 | 2 | 4 |
| A54 | 1.0 | 3 | 4 | 3 | 2 | 2 | 2 | 4 | 0 | 2 | 1 | 2 | 2 |
| A55 | 1.0 | 2 | 4 | 3 | 2 | 2 | 3 | 4 | 0 | 2 | 2 | 1 | 3 |
| A56 | 1.0 | 3 | 4 | 2 | 2 | 2 | 4 | 0 | 2 | 2 | 1 | 3 |   |
| A63 | 0.5 | 1 | 4 | 1 | 4 | 4 | 3 | 2 | 2 | 0 | 2 | 3 |   |
| A65 | 0.5 | 1 | 4 | 2 | 4 | 2 | 3 | 3 | 2 | 1 | 2 | 2 | 2 |
| C1 | 1.0 | 0 | 4 | 4 | 2 | 0 | 3 | 3 | 2 | 3 | 1 | 1 | 2 |

| Ex | Kg/ha | a | b | c | d | e | f | g | h | i | j | k | l |
|---|---|---|---|---|---|---|---|---|---|---|---|---|---|
| C2 | 1.0 | 2 | 4 | 2 | 0 | 0 | 1 | 3 | 1 | 1 | 2 | 2 | 4 |
| C3 | 1.0 | — | 4 | 4 | 2 | 2 | 1 | 4 | 0 | 2 | 2 | 1 | 2 |
| C4 | 1.0 | 3 | 3 | 2 | 2 | 2 | 2 | 3 | 1 | 2 | 2 | 2 | 2 |
| C5 | 0.5 | 2 | 4 | 3 | 3 | 2 | 3 | 3 | 2 | 1 | 1 | 2 | 3 |
| C6 | 0.5 | 2 | 4 | 3 | 2 | 2 | 2 | 3 | 2 | 2 | 2 | 1 | 2 |
| E2 | 1.0 | 3 | 3 | 3 | 3 | 2 | 2 | 2 | 0 | 2 | 2 | 1 | 3 |

We claim:

1. A compound selected from the group consisting of the triazole sulphonamides of the formula:

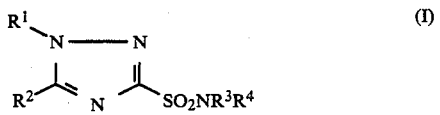

or a salt thereof, where:

R$^1$ represents phenyl (unsubstituted or substituted by halogen or alkyl or alkoxy of 1 to 4 carbon atoms) or monocyclic nitrogen-carbon heterocyclyl selected from the group consisting of pyrimidinyl, triazinyl, thiadiazolyl, pyrazinyl and pyridinyl (unsubstituted or substituted by alkyl, alkoxy or alkylthio of 1 to 4 carbon atoms, cyano, halogen, alkylsulphinyl or alkylsulphonyl of 1 to 4 carbon atoms, or amino which may itself be substituted by methyl or ethyl);

R$^2$ represents hydrogen, halogen, cyano, amino, alkylamino or dialkylamino (in which each alkyl moiety is of 1 to 4 carbon atoms), alkyl or alkoxy of 1 to 6 carbon atoms (unsubstituted or substituted by halogen, hydroxy, alkoxy of 1 to 4 carbon atoms or alkanoyl-oxy of 2 to 5 carbon atoms), alkoxycarbonyl of 2 to 5 carbon atoms, or pyrrolyl which is unsubstituted or substituted by alkyl of 1 to 4 carbon atoms:

R$^3$ represents a phenyl group substituted by halogen, nitro, cyano, alkoxycarbonyl of 2 to 6 carbon atoms, or by alkyl, alkoxy or alkylthio of 1 to 4 carbon atoms which may be further substituted by halogen; and R$^4$ represents hydrogen, alkyl of 1 to 6 carbon atoms, alkanoyl of 1 to 6 carbon atoms, benzoyl, alkylsulphonyl of 1 to 6 carbon atoms, alkoxycarbonyl in which the alkyl moiety is of 1 to 6 carbon atoms, dimethylcarbamoyl or benzyl.

2. The triazole sulphonamide according to claim 1 in which R$^1$ represents phenyl, 3,5-dimethylphenyl, 4-methylpyrimidin-2-yl, 4-methoxypyrimidin-2-yl, 4,6-dimethylpyrimidin-2-yl, 4,6-dimethoxypyrimidin-2-yl, 4,6-dichloropyrimidin-2-yl, 4-methyl-6-chloropyrimidin-2-yl, 4-methyl-6-methylaminopyrimidin-2-yl, 4-methyl-6-aminopyrimidin-2-yl, 4-methyl-6-dimethylaminopyrimidin-2-yl, 4-chloro-6-methoxypyrimidin-2-yl, 4-methyl-5-chloro-6-methoxypyrimidin-2-yl, 4-methyl-6-methoxypyrimidin-2-yl, 4,6-dimethoxy-1,3,5-triazin-2-yl, 4-chloro-6-methyl-1,3,5-triazin-2-yl, 4-chloro-6-methoxy-1,3,5-triazin-2-yl, 4-methoxy-6-methyl-1,3,5-triazin-2-yl, 4-methylamino-6-methoxy-1,3,5-triazin-2-yl or 4-methylamino-6-chloro-1,3,5-triazin-2-yl.

3. The triazole sulphonamide according to claim 1 in which R$^2$ represents hydrogen, chloro, bromo, cyano, methyl, ethyl, n-propyl, n-butyl, s-butyl, hydroxymethyl, methoxymethyl, ethoxymethyl, methoxyethyl, acetoxymethyl, methoxy, ethoxy, methoxycarbonyl, amino, methylamino, ethylamino, pyrrol-1-yl or 2,5-dimethylpyrrol-1-yl.

4. The triazole sulphonamide according to claim 1 in which R$^3$ represents 2-fluorophenyl, 2-chlorophenyl, 2-bromophenyl, 2-cyanophenyl, 2-methylphenyl, 2-methoxyphenyl, 2-methylthiophenyl, 2-trifluoromethylphenyl, 2-methoxycarbonylphenyl, 2-ethoxycarbonylphenyl, 3-fluorophenyl, 2-difluoromethoxyphenyl, 2,3-difluorophenyl, 2,5-difluorophenyl, 2,6-dimethylphenyl, 2,3,5,6-tetrafluorophenyl, 2-methyl-6-methoxycarbonylphenyl, 2-fluoro-6-methoxycarbonylphenyl, 2,6-difluorophenyl, 2,6-dichlorophenyl, 2,6-dibromophenyl, 2-methyl-6-nitrophenyl, 2-chloro-6-methylphenyl, 2-fluoro-6-methoxycarbonylphenyl, 2-chloro-6-methoxycarbonylphenyl, 2,6-dichloro-3-methylphenyl or 2-chloro-6-fluorophenyl.

5. The triazole sulphonamide according to claim 1 in which R$^4$ represents hydrogen, methyl, acetyl, benzoyl, methylsulphonyl, methoxycarbonyl, dimethylcarbamoyl or benzyl.

6. A triazole sulphonamide according to claim 1 which is: N-(2,6-difluorophenyl)-1-(pyrimidin-2-yl)-5-methyl-1,2,4-triazole-3-sulphonamide; N-(2,6-dichloro-3-methylphenyl)-1-(pyrimidin-2-yl)-5-methyl-1,2,4-triazole-3-sulphonamide; N-(2-methyl-6-nitrophenyl)-1-(pyrimidin-2-yl)-5-methyl-1,2,4-triazole-3-sulphonamide; N-(2,6-difluorophenyl)-1-(4,6-dimethylpyrimidin-2-yl)-5-methyl-1,2,4-triazole-3-sulphonamide N-(2,6-dichlorophenyl)-1-(pyrimidin-2-yl)-5-methyl-1,2,4-triazole-3-sulphonamide; N-(2,6-difluorophenyl)-1-(4-methylpyrimidin-2-yl)-5-methyl-1,2,4-triazole-3-sulphonamide; N-(2,6-difluorophenyl)-1-(4-methoxy-6-methylpyrimidin-2-yl)-5-methyl-1,2,4-triazole-3-sulphonamide; N-(2,6-dichlorophenyl)-1-(4,6-dimethoxy-1,3,5-triazin-2-yl)-5-methyl-1,2,4-triazole-3-sulphonamide; N-(2,6-dichlorophenyl)-1-(4,6-dimethylpyrimidin-2-yl)-1,2,4-triazole-3-sulphonamide; N-(2,6-dichlorophenyl)-1-(4,6-dimethylpyrimidin-2-yl)-5-methyl-1,2,4-triazole-3-sulphonamide; N-(2-methyl-6-nitrophenyl)-1-(4,6-dimethylpyrimidin-2-yl)-5-methyl-1,2,4-triazole-3-sulphonamide; N-(2,6-dichlorophenyl)-5-(2,5-dimethylpyrrol-1-yl)-1,2,4-triazole-3-sulphonamide; N-(2,6-difluorophenyl)-5-(2,5-dimethylpyrrol-1-yl)-1,2,4-triazole-3-sulphonamide; N-(2,6-dichloro-3-methylphenyl)-1-(4,6-dimethylpyrimidin-2-yl)-1,2,4-triazole-3-sulphonamide; N-(2,6-dichlorophenyl)-5-amino-1-(4,6-dimethylpyrimidin-2-yl)-1,2,4-triazole-3-sulphonamide; or N-(2,6-dichloro-3-methylphenyl)-5-amino-1-(4,6-dimethoxy-1,3,5-triazin-2-yl)-1,2,4-triazole-3-sulphonamide.

7. The triazole sulphonamide according to claim 4 in which R$^4$ represents hydrogen, methyl, acetyl, benzoyl, methylsulphonyl, methoxycarbonyl, dimethylcarbamoyl or benzyl.

8. The triazole sulphonamide according to claim 7, in which R$^2$ represents hydrogen, chloro, bromo, cyano, methyl, ethyl, n-propyl, n-butyl, sec-butyl, hydroxymethyl, methoxymethyl, ethoxymethyl, methoxyethyl, acetoxymethyl, methoxy, ethoxy, methoxycarbonyl, amino, methylamino, ethylamino, pyrrol-1-yl or 2,5-dimethylpyrrol-1-yl.

9. A triazole sulphonamide according to claim 1 in which R$^1$ is a substituted or unsubstituted pyrimidin-2-yl group.

10. A triazole sulphonamide according to claim 9, in which R$^2$ represents hydrogen, chloro, bromo, cyano, methyl, ethyl, n-propyl, n-butyl, sec-butyl, hydroxymethyl, methoxymethyl, ethoxymethyl, methoxyethyl, acetoxymethyl, methoxy, ethoxy or methoxycarbonyl.

11. A herbicidal composition which comprises one or more triazole sulphonamides according to claim 1, in association with a suitable carrier and/or surface active agent.

12. A herbicidal composition which comprises one or more triazole sulphonamides according to claim 2, in association with a suitable carrier and/or surface agent.

13. A herbicidal composition which comprises one or more triazole sulphonamides according to claim 3, in association with a suitable carrier and/or surface agent.

14. A herbicidal composition which comprises one or more triazole sulphonamides according to claim 4, in association with a suitable carrier and/or surface agent.

15. A herbicidal composition which comprises one or more triazole sulphonamides according to claim 5, in association with a suitable carrier and/or surface agent.

16. A herbicidal composition which comprises one or more triazole sulphonamides according to claim 6, in association with a suitable carrier and/or surface agent.

17. A herbicidal composition which comprises one or more triazole sulphonamide according to claim 10, in association with a suitable carrier and/or surface agent.

18. A herbicidal composition which comprises one or more triazole sulphonamide according to claim 9, in association with a suitable carrier and/or surface agent.

* * * * *